(12) United States Patent
Bala et al.

(10) Patent No.: US 9,056,867 B2
(45) Date of Patent: Jun. 16, 2015

(54) N-SUBSTITUTED HETEROCYCLYL CARBOXAMIDES

(75) Inventors: Kamlesh Jagdis Bala, Horsham (GB); Emma Budd, Horsham (GB); Lee Edwards, Horsham (GB); Catherine Howsham, Horsham (GB); Darren Mark LeGrand, Horsham (GB); Roger John Taylor, Horsham (GB)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/345,022

(22) PCT Filed: Sep. 14, 2012

(86) PCT No.: PCT/IB2012/054832
§ 371 (c)(1),
(2), (4) Date: Mar. 14, 2014

(87) PCT Pub. No.: WO2013/038390
PCT Pub. Date: Mar. 21, 2013

(65) Prior Publication Data
US 2014/0323485 A1 Oct. 30, 2014

Related U.S. Application Data

(60) Provisional application No. 61/535,671, filed on Sep. 16, 2011.

(51) Int. Cl.
| | |
|---|---|
| A61K 31/4427 | (2006.01) |
| C07D 487/04 | (2006.01) |
| A61K 31/415 | (2006.01) |
| A61K 31/4439 | (2006.01) |
| A61K 31/497 | (2006.01) |
| A61K 45/06 | (2006.01) |
| A61K 31/4985 | (2006.01) |
| A61K 31/5377 | (2006.01) |
| A61K 31/444 | (2006.01) |
| C07D 231/40 | (2006.01) |
| C07D 401/12 | (2006.01) |
| C07D 401/14 | (2006.01) |
| C07D 403/12 | (2006.01) |
| C07D 413/14 | (2006.01) |

(52) U.S. Cl.
CPC ............ *C07D 487/04* (2013.01); *A61K 31/415* (2013.01); *A61K 31/4439* (2013.01); *A61K 31/497* (2013.01); *A61K 45/06* (2013.01); *A61K 31/4985* (2013.01); *A61K 31/5377* (2013.01); *A61K 31/444* (2013.01); *C07D 231/40* (2013.01); *C07D 401/12* (2013.01); *C07D 401/14* (2013.01); *C07D 403/12* (2013.01); *C07D 413/14* (2013.01)

(58) Field of Classification Search
CPC .......................... C07D 401/12; C07D 401/14
See application file for complete search history.

(56) References Cited

U.S. PATENT DOCUMENTS

| | | |
|---|---|---|
| 3,573,306 A | 3/1971 | Shepard et al. |
| 4,537,899 A | 8/1985 | Horvath et al. |
| 8,247,436 B2 | 8/2012 | Baettig et al. |
| 8,476,269 B2 | 7/2013 | Baettig et al. |
| 2014/0171412 A1 | 6/2014 | Ahmed et al. |
| 2014/0171417 A1 | 6/2014 | Ahmed et al. |
| 2014/0228376 A1 | 8/2014 | Bala et al. |
| 2015/0045364 A1 | 2/2015 | Baettig et al. |

FOREIGN PATENT DOCUMENTS

| | | |
|---|---|---|
| DE | 10148617 | 4/2003 |
| DE | 10219294 | 11/2003 |
| EP | 2280001 | 2/2011 |
| WO | WO 96/14843 | 5/1996 |
| WO | WO 98/14450 | 4/1998 |

(Continued)

OTHER PUBLICATIONS

Bossi et al., "Crystal Structures of Anaplastic Lymphoma Kinase in Complex with ATP Competitive Inhibitors" *Biochemistry* 49(32):6813-6825, 2010.
Raffa et al., "Synthesis and Antifungal Activity of New *N*-(1-phenyl-4-carbetoxypyrazol-5-y1)-, *N*(indazol-3-yl)- and *N*-(indazol-5-y1)-2-iodobenzamides" *Farmaco* 57(3):183-187, 2002.
Raffa et al., "Synthesis and Antiproliferative Activity and Novel 3-(Indazol-3-y1)-quinazolin-4(3*H*)-one and 3-(Indazol-3-y1)-benzotriazin-4(3*H*)-one Derivatives" *Arch Pharm Pharm Med Chem* 332:317-320, 1999.
Plescia et al., "Synthesis and Biological Evaluation of New Indazole Derivatives" *ARKIVOC* (x) 163-177, 2010.
Daidone et al., "Synthesis, Crystallographic Studies and Biological Evaluation of Some 2-Substituted 3-Indazoly1-4(3*H*)-Quinazolinones and 3-Indazoly1-4(3*H*)-Benzotriazioneses" *Heterocycles* 43(11):2385-2396, 1996.

(Continued)

*Primary Examiner* — Brian McDowell
(74) *Attorney, Agent, or Firm* — Qian Zhang

(57) ABSTRACT

A compound of Formula I and pharmaceutically acceptable salts and solvates thereof, wherein $R^1, R^2, R^3, R^a$, A, B, D and E are all as defined herein. The compounds modulate the activity of CFTR and are useful in the treatment of inflammatory or obstructive airways diseases or mucosal hydration, including, for example cystic fibrosis. Pharmaceutical compositions that contain the compounds and processes for preparing the compounds are also described.

10 Claims, No Drawings

(56) References Cited

FOREIGN PATENT DOCUMENTS

| | | |
|---|---|---|
| WO | WO 01/85726 | 11/2001 |
| WO | WO 02/00651 | 1/2002 |
| WO | WO 02/066470 | 8/2002 |
| WO | WO 03/029223 | 4/2003 |
| WO | WO 03/078403 | 9/2003 |
| WO | WO 03/093297 | 11/2003 |
| WO | WO 2004/055006 | 7/2004 |
| WO | WO 2006/091428 | 8/2006 |
| WO | WO 2006/126695 | 11/2006 |
| WO | WO 2007/009898 | 6/2007 |
| WO | WO 2007/068619 | 6/2007 |
| WO | WO 2007/068637 | 6/2007 |
| WO | WO 2007/099171 | 9/2007 |
| WO | WO 2007/138017 | 12/2007 |
| WO | WO 2008/043745 | 4/2008 |
| WO | WO 2008/074749 | 6/2008 |
| WO | WO 2008/089307 | 7/2008 |
| WO | WO 2008/089310 | 7/2008 |
| WO | WO 2009/013126 | 1/2009 |
| WO | WO 2009/042294 | 4/2009 |
| WO | WO 2009/076593 | 6/2009 |
| WO | WO 2009/078992 | 6/2009 |
| WO | WO 2009/108657 | 9/2009 |
| WO | WO 2009/110985 | 9/2009 |
| WO | WO 2009/123896 | 10/2009 |
| WO | WO 2009/143039 | 11/2009 |
| WO | WO 2009/149837 | 12/2009 |
| WO | WO 2010/026262 | 3/2010 |
| WO | WO 2010/034838 | 4/2010 |
| WO | WO 2010/046780 | 4/2010 |
| WO | WO 2010/054398 | 5/2010 |
| WO | WO 2010/069966 | 6/2010 |
| WO | WO 2010/071837 | 6/2010 |
| WO | WO 2010/073011 | 7/2010 |
| WO | WO 2010/094695 | 8/2010 |
| WO | WO 2010/101964 | 9/2010 |
| WO | WO 2010/132404 | 11/2010 |
| WO | WO 2011/041593 | 4/2011 |
| WO | WO 2011/050325 | 4/2011 |
| WO | WO 2011/113894 | 9/2011 |
| WO | WO 2013/038386 | 3/2013 |
| WO | 2014/097147 A1 | 6/2014 |
| WO | 2014/097148 A1 | 6/2014 |

OTHER PUBLICATIONS

Plescia et al., "Novel Ring Systems. Pyrazolo[1,5-c][1,3,5]benzotriazocin-5(4*H*)one and Pyrazol[1,5-c][1,2,3,5]benzoletrazocin-5(4*H*)one Derivatives" *Journal of Heterocyclic Chemistry* 12:199-202, 1975.

Plescia et al., Atti della Accademia di Scienze, Lettere e Arti di Palermo, Parte 1: Scienze (1974), Volume Date 1973, 33(2), 301-304.

Lazaro et al., "Systemes aromatiques a 10 electrons pi derives de l'aza-3a pentalene. XXXII Recherches dans la serie du pyrazolo [1,5-alpha]benzimidazole" *Journal of Heterocyclic Chemistry* 15:715-720, 1978.

Gavrilenko et al., "Synthesis and Properties of 3-amino-3-pyrazolin-5-ones" *Journal of Organic Chemistry* 40(19):2720-2724, 1975.

Daidone et al., "N-Pirazolil-2-Nitrobenzammidi ad Attivita Antifungina" *Farmaco, Edizione Scientifica* 41(5), 408-416, 1986.

Peet et al., "3-(1*H*-Tetrazol-5-y1)-*4*(3H)-quinazolinone Sodium Salt (MDL 427): A New Antiallergic Agent" *Journal of Medicinal Chemistry* 29(11):2403-2409, 1986.

Shepard et al., "Carboxylic *N, N*-Diphenylcarbamic Anhydrides. New Acylating Agents(1)" *Journal of Heterocyclic Chemistry* 16(2):321-325, 1979.

Shepard et al. "3,5-Diamino-6-Chloropyrazinecarboxylic and Active Esters and Their Reactions (1)" *Tetrahedron Letters* 54:4757-4760, 1969.

Cook et al., "Derivatives of Triaza-Indolizines" *Recueil* 69:343-35, 1950.

N-SUBSTITUTED HETEROCYCLYL CARBOXAMIDES

CROSS-REFERENCE TO RELATED APPLICATIONS

This application is the U.S. National Stage of International Application No. PCT/IB2012/054832, filed Sep. 14, 2012, which claims the benefit of priority to U.S. Provisional Application No. 61/535,671, filed Sep. 16, 2011, the contents of which are incorporated herein by reference.

This invention relates to N-substituted heterocyclyl carboxamides, their preparation and use as pharmaceuticals. In particular, N-substituted heterocyclyl carboxamides which modulate the activity of CFTR and are useful in the treatment of inflammatory or obstructive airways diseases or mucosal hydration, including, for example cystic fibrosis.

In one aspect, the invention provides compounds according to Formula I:

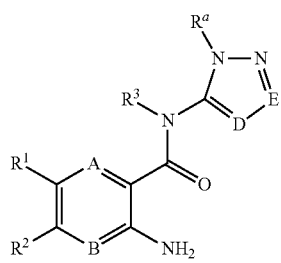

(I)

or a pharmaceutically acceptable salt or solvate thereof, wherein:
A is N or $CR^4$;
B is N or $CR^6$;
D is N or $CR^6$;
E is N or $CR^7$, provided that D and E are not both N;
$R^1$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; halogen; $SO_2NR^8R^9$; $SO_2R^{10}$; S—$C_1$-$C_8$ alkyl optionally substituted by one or more halogen atoms; S—$C_6$-$C_{14}$ aryl optionally substituted by one or more Z substituents; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; CN; $NR^{11}R^{12}$; $CONR^{13}R^{14}$; $NR^{13}SO2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;
$R^2$ is selected from $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; Cl; Br; I; $SO_2NR^8R^9$; $SO_2R^{10}$; S—$C_1$-$C_8$ alkyl optionally substituted by one or more halogen atoms; S—$C_6$-$C_{14}$ aryl; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; CN; $CONR^{13}R^{14}$; $NR^{13}SO2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;
$R^a$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $SO_2R^{10}$; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; $C(O)R^{15}$ and $CO_2R^{15}$, wherein the cycloalkyl, cycloalkenyl, aryl and heterocyclyl groups are each optionally substituted by one or more Z substituents;
$R^3$ and $R^4$ are each independently selected from H and $C_1$-$C_8$ alkyl optionally substituted by one or more halogen atoms;
$R^5$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; cycloalkenyl; —$C_1$-$C_4$ alkyl-$C_3$-$C_8$ cycloalkyl; halogen; —($C_0$-$C_4$ alkyl)-$C_6$-$C_{14}$ aryl; and —($C_0$-$C_4$ alkyl)-3 to 14 membered heterocyclic group, wherein the heterocyclic group contains at least one heteroatom selected from N, O and S; wherein the cycloalkyl, cycloalkenyl, aryl and heterocyclyl groups are each optionally substituted by one or more Z substituents;
$R^6$ and $R^7$ are each independently selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; and —($C_0$-$C_4$ alkyl)-$CO_2R^{15}$, wherein the cycloalkyl, cycloalkenyl, aryl and heterocyclyl groups are each optionally substituted by one or more Z substituents; or
$R^6$ and $R^7$ are each independently a group of the formula:

—$(CH_2)_n$—X—$(CH_2)_m$—$NR^{17}R^{18}$; or $R^6$ and $R^7$ together with the carbon atoms to which they are bound form a 5 to 8 membered carbocyclic ring system or a 5 to 8 membered heterocyclic ring system containing one or more heteroatoms selected from N, O and S, wherein the ring system is optionally substituted by one or more Z substituents;
X is absent, O, S, CO, SO, $SO_2$ or $CH_2$;
n and m are each independently selected from 0, 1, 2 and 3;
$R^8$, $R^{11}$, $R^{13}$ and $R^{17}$ are each independently selected from H, $C_1$-$C_8$ alkyl optionally substituted by one or more halogen atoms, $C_3$-$C_{10}$ cycloalkyl and —($C_1$-$C_4$ alkyl)-$C_3$-$C_8$ cycloalkyl;
$R^9$, $R^{10}$, $R^{12}$, $R^{14}$, $R^{15}$, $R^{16}$ and $R^{18}$ are each independently selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; and —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or
$R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;
Z is independently selected from OH; aryl; O-aryl; benzyl; O-benzyl; $C_1$-$C_6$ alkyl optionally substituted by one or more OH groups or $NH_2$ groups; $C_1$-$C_6$ alkyl optionally substituted by one or more halogen atoms; $C_1$-$C_6$ alkoxy optionally substituted by one or more OH groups or $C_1$-$C_4$ alkoxy; $NR^{18}(SO_2)R^{21}$; $(SO_2)NR^{19}R^{21}$; $(SO_2)R^{21}$; $NR^{18}C(O)R^{21}$; $C(O)NR^{19}R^{21}$; $NR^{19}C(O)NR^{19}R^{21}$; $NR^{18}C(O)OR^{19}$; $NR^{19}R^{21}$;

C(O)OR$^{19}$; C(O)R$^{19}$; SR$^{19}$; OR$^{19}$; oxo; CN; NO$_2$; halogen; and —(C$_0$-C$_4$ alkyl)-3 to 14 membered heterocyclic group, wherein the heterocyclic group contains at least one heteroatom selected from N, O and S, optionally substituted by one or more groups selected from halogen, oxo, C$_1$-C$_6$ alkyl and C(O)C$_1$-C$_6$ alkyl;

R$^{18}$ and R$^{20}$ are each independently selected from H and C$_1$-C$_6$ alkyl;

R$^{19}$ and R$^{21}$ are each independently selected from H; C$_1$-C$_8$ alkyl; C$_3$-C$_8$ cycloalkyl; C$_1$-C$_4$ alkoxy-C$_1$-C$_4$ alkyl; (C$_0$-C$_4$ alkyl)-aryl optionally substituted by one or more groups selected from C$_1$-C$_6$ alkyl, C$_1$-C$_6$ alkoxy and halogen; (C$_0$-C$_4$ alkyl)- 3- to 14-membered heterocyclic group, the heterocyclic group including one or more heteroatoms selected from N, O and S, optionally substituted by one or more groups selected from halogen, oxo, C$_1$-C$_6$ alkyl and C(O)C$_1$-C$_6$ alkyl; (C$_0$-C$_4$ alkyl)-O-aryl optionally substituted by one or more groups selected from C$_1$-C$_6$ alkyl, C$_1$-C$_6$ alkoxy and halogen; and (C$_0$-C$_4$ alkyl)- O-3- to 14-membered heterocyclic group, the heterocyclic group including one or more heteroatoms selected from N, O and S, optionally substituted by one or more groups selected from halogen, C$_1$-C$_6$ alkyl and C(O)C$_1$-C$_6$ alkyl; wherein the alkyl groups are optionally substituted by one or more halogen atoms, C$_1$-C$_4$ alkoxy, C(O)NH$_2$, C(O)NHC$_1$-C$_6$ alkyl or C(O)N(C$_1$-C$_6$ alkyl)$_2$; or R$^{19}$ and R$^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; S(O)$_2$-aryl; S(O)$_2$—C$_1$-C$_6$ alkyl; C$_1$-C$_6$ alkyl optionally substituted by one or more halogen atoms; C$_1$-C$_6$ alkoxy optionally substituted by one or more OH groups or C$_1$-C$_4$ alkoxy; and C(O)OC$_1$-C$_6$ alkyl, wherein the aryl and heterocyclic substituent groups are themselves optionally substituted by C$_1$-C$_6$ alkyl, C$_1$-C$_6$ haloalkyl or C$_1$-C$_6$ alkoxy;

for use in the treatment of a disease or disorder mediated by CFTR.

In a second aspect, the invention provides compounds according to Formula I:

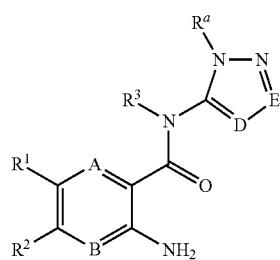

(I)

or a pharmaceutically acceptable salt or solvate thereof, wherein:
A is N or CR$^4$;
B is N or CR$^5$;
D is N or CR$^6$;
E is N or CR$^7$, provided that:
i) D and E are not both N; and
ii) either A or B, or both, is N;
R$^1$ is selected from H; C$_1$-C$_8$ alkyl optionally substituted by one or more halogen atoms; C$_2$-C$_8$ alkenyl; C$_2$-C$_8$ alkynyl; C$_3$-C$_{10}$ cycloalkyl; C$_5$-C$_{10}$ cycloalkenyl; —C$_1$-C$_4$ alkyl-C$_3$-C$_8$ cycloalkyl; C$_1$-C$_8$ alkoxy optionally substituted by one or more halogen atoms; OH; halogen; SO$_2$NR$^8$R$^9$; SO$_2$R$^{10}$; S—C$_1$-C$_8$ alkyl optionally substituted by one or more halogen atoms; S—C$_6$-C$_{14}$ aryl optionally substituted by one or more Z substituents; —(C$_0$-C$_4$ alkyl)-C$_6$-C$_{14}$ aryl; —(C$_0$-C$_4$ alkyl)-3 to 14 membered heterocyclic group, wherein the heterocyclic group contains at least one heteroatom selected from N, O and S; CN; NR$^{11}$R$^{12}$; CONR$^{13}$R$^{14}$; NR$^{13}$SO2R$^{15}$; NR$^{13}$C(O)R$^{15}$ and CO$_2$R$^{15}$, wherein the cycloalkyl, cycloalkenyl, aryl and heterocyclyl groups are each optionally substituted by one or more Z substituents;

R$^2$ is selected from C$_1$-C$_8$ alkyl optionally substituted by one or more halogen atoms; C$_2$-C$_8$ alkenyl; C$_2$-C$_8$ alkynyl; C$_3$-C$_{10}$ cycloalkyl; C$_5$-C$_{10}$ cycloalkenyl; —C$_1$-C$_4$ alkyl-C$_3$-C$_8$ cycloalkyl; C$_1$-C$_8$ alkoxy optionally substituted by one or more halogen atoms; OH; Cl; Br; I; SO$_2$NR$^8$R$^9$; SO$_2$R$^{10}$; S—C$_1$-C$_8$ alkyl optionally substituted by one or more halogen atoms; S—C$_6$-C$_{14}$ aryl; —(C$_0$-C$_4$ alkyl)-C$_6$-C$_{14}$ aryl; —(C$_0$-C$_4$ alkyl)-3 to 14 membered heterocyclic group, wherein the heterocyclic group contains at least one heteroatom selected from N, O and S; CN; CONR$^{13}$R$^{14}$; NR$^{13}$SO2R$^{15}$; NR$^{13}$C(O)R$^{15}$ and CO$_2$R$^{15}$, wherein the cycloalkyl, cycloalkenyl, aryl and heterocyclyl groups are each optionally substituted by one or more Z substituents;

R$^a$ is selected from H; C$_1$-C$_8$ alkyl optionally substituted by one or more halogen atoms; C$_2$-C$_8$ alkenyl; C$_2$-C$_8$ alkynyl; cycloalkyl; cycloalkenyl; —C$_1$-C$_4$ alkyl-C$_3$-C$_8$ cycloalkyl; SO$_2$R$^{10}$; —(C$_0$-C$_4$ alkyl)-C$_6$-C$_{14}$ aryl; —(C$_0$-C$_4$ alkyl)-3 to 14 membered heterocyclic group, wherein the heterocyclic group contains at least one heteroatom selected from N, O and S; C(O)R$^{15}$ and CO$_2$R$^{15}$, wherein the cycloalkyl, cycloalkenyl, aryl and heterocyclyl groups are each optionally substituted by one or more Z substituents;

R$^3$ and R$^4$ are each independently selected from H and C$_1$-C$_8$ alkyl optionally substituted by one or more halogen atoms;

R$^5$ is selected from H; C$_1$-C$_8$ alkyl optionally substituted by one or more halogen atoms; C$_2$-C$_8$ alkenyl; C$_2$-C$_8$ alkynyl; C$_3$-C$_{10}$ cycloalkyl; cycloalkenyl; —C$_1$-C$_4$ alkyl-C$_3$-C$_8$ cycloalkyl; halogen; —(C$_0$-C$_4$ alkyl)-C$_6$-C$_{14}$ aryl; and —(C$_0$-C$_4$ alkyl)-3 to 14 membered heterocyclic group, wherein the heterocyclic group contains at least one heteroatom selected from N, O and S; wherein the cycloalkyl, cycloalkenyl, aryl and heterocyclyl groups are each optionally substituted by one or more Z substituents;

R$^6$ and R$^7$ are each independently selected from H; C$_1$-C$_8$ alkyl optionally substituted by one or more halogen atoms; C$_2$-C$_8$ alkenyl; C$_2$-C$_8$ alkynyl; C$_5$-C$_{10}$ cycloalkyl; cycloalkenyl; —C$_1$-C$_4$ alkyl-C$_3$-C$_8$ cycloalkyl; C$_1$-C$_8$ alkoxy optionally substituted by one or more halogen atoms; OH; CN; halogen; —(C$_0$-C$_4$ alkyl)-C$_6$-C$_{14}$ aryl; —(C$_0$-C$_4$ alkyl)-3 to 14 membered heterocyclic group, wherein the heterocyclic group contains at least one heteroatom selected from N, O and S; and —(C$_0$-C$_4$ alkyl)-CO$_2$R$^{15}$, wherein the cycloalkyl, cycloalkenyl, aryl and heterocyclyl groups are each optionally substituted by one or more Z substituents; or R$^6$ and R$^2$ are each independently a group of the formula:

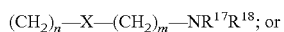

(CH$_2$)$_n$—X—(CH$_2$)$_m$—NR$^{17}$R$^{18}$; or

R$^6$ and R$^7$ together with the carbon atoms to which they are bound form a 5 to 8 membered carbocyclic ring system or a 5 to 8 membered heterocyclic ring system containing one or more heteroatoms selected from N, O and S, wherein the ring system is optionally substituted by one or more Z substituents;

X is absent, O, S, CO, SO, SO$_2$ or CH$_2$;

n and m are each independently selected from 0, 1, 2 and 3;

$R^8$, $R^{11}$, $R^{13}$ and $R^{17}$ are each independently selected from H, $C_1$-$C_8$ alkyl optionally substituted by one or more halogen atoms, $C_3$-$C_{10}$ cycloalkyl and —($C_1$-$C_4$ alkyl)-$C_3$-$C_8$ cycloalkyl;

$R^9$, $R^{10}$, $R^{12}$, $R^{14}$, $R^{15}$, $R^{16}$ and $R^{18}$ are each independently selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; and —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;

Z is independently selected from OH; aryl; O-aryl; benzyl; O-benzyl; $C_1$-$C_6$ alkyl optionally substituted by one or more OH groups or $NH_2$ groups; $C_1$-$C_6$ alkyl optionally substituted by one or more halogen atoms; $C_1$-$C_6$ alkoxy optionally substituted by one or more OH groups or $C_1$-$C_4$ alkoxy; $NR^{18'}(SO_2)R^{21}$; $(SO_2)NR^{19}R^{21}$; $(SO_2)R^{21}$; $NR^{18'}C(O)R^{21}$; $C(O)NR^{19}R^{21}$; $NR^{19}C(O)NR^{19}R^{21}$; $NR^{18'}C(O)OR^{19}$; $NR^{19}R^{21}$; $C(O)OR^{19}$; $C(O)R^{19}$; $SR^{19}$; $OR^{19}$; oxo; CN; $NO_2$; halogen; and —($C_0$-$C_4$ alkyl)-3 to 14 membered heterocyclic group, wherein the heterocyclic group contains at least one heteroatom selected from N, O and S, optionally substituted by one or more groups selected from halogen, oxo, $C_1$-$C_6$ alkyl and $C(O)C_1$-$C_6$ alkyl;

$R^{18'}$ and $R^{20}$ are each independently selected from H and $C_1$-$C_8$ alkyl;

$R^{19}$ and $R^{21}$ are each independently selected from H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)- 3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)- O-3- to 14-membered heterocyclic group, the heterocyclic group including one or more heteroatoms selected from N, O and S, optionally substituted by one or more groups selected from halogen, $C_1$-$C_6$ alkyl and $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

Unless specified otherwise, the term "compounds of the present invention" refers to compounds of Formula (I) and subformulae thereof, prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

For purposes of interpreting this specification, the following definitions will apply and whenever appropriate, terms used in the singular will also include the plural and vice versa.

"Optionally substituted" means the group referred to can be substituted at one or more positions by any one or any combination of the radicals listed thereafter.

"optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_8$-Alkyl", as used herein, denotes straight chain or branched alkyl having 1-8 carbon atoms. If a different number of carbon atoms is specified, such as $C_6$ or $C_3$, then the definition is to be amended accordingly.

"$C_1$-$C_8$-Alkoxy", as used herein, denotes straight chain or branched alkoxy having 1-8 carbon atoms. If a different number of carbon atoms is specified, such as $C_6$ or $C_3$, then the definition is to be amended accordingly.

The term "alkylene" denotes a straight chain or branched saturated hydrocarbon chain containing between 1 and 8 carbon atoms. If a different number of carbon atoms is specified, such as $C_6$ or $C_3$, then the definition is to be amended accordingly.

"Amino-$C_1$-$C_8$-alkyl" and "amino-$C_1$-$C_8$-alkoxy" denote amino attached by a nitrogen atom to $C_1$-$C_8$-alkyl, e.g., $NH_2$—($C_1$-$C_8$)—, or to $C_1$-$C_8$-alkoxy, e.g., $NH_2$—($C_1$-$C_8$)—O—. If a different number of carbon atoms is specified, such as $C_6$ or $C_3$, then the definition is to be amended accordingly.

"$C_1$-$C_8$-Alkylamino" and "di($C_1$-$C_8$-alkyl)amino" denote $C_1$-$C_8$-alkyl, as hereinbefore defined, attached by a carbon atom to an amino group. The $C_1$-$C_8$-alkyl groups in di($C_1$-$C_8$-alkyl)amino may be the same or different. If a different number of carbon atoms is specified, such as $C_6$ or $C_3$, then the definition is to be amended accordingly.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl. If a different number of carbon atoms is specified, such as $C_6$ or $C_3$, then the definition is to be amended accordingly.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined, attached by a carbon atom to a carbonyl group. If a different number of carbon atoms is specified, such as $C_6$ or $C_3$, then the definition is to be amended accordingly.

"$C_3$-$C_8$-Cycloalkylcarbonyl", as used herein, denotes $C_3$-$C_8$-cycloalkyl, as hereinbefore defined, attached by a carbon atom to a carbonyl group. If a different number of carbon atoms is specified, such as $C_6$ or $C_3$, then the definition is to be amended accordingly.

"$C_7$-$C_{14}$-Aralkyl", as used herein, denotes alkyl, e.g., $C_1$-$C_4$-alkyl, as hereinbefore defined, substituted by a $C_6$-$C_{10}$-aromatic carbocyclic group, as herein defined. If a different number of carbon atoms is specified, such as $C_6$ or $C_3$, then the definition is to be amended accordingly.

"$C_3$-$C_{15}$-Carbocyclic group", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl. If a different number of carbon atoms is specified, such as $C_6$, then the definition is to be amended accordingly.

"aryl" or "$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_{10}$, then the definition is to be amended accordingly.

"4- to 8-Membered heterocyclic group", "5- to 6-membered heterocyclic group", "3- to 10-membered heterocyclic group", "3- to 14-membered heterocyclic group", "4- to 14-membered heterocyclic group" and "5- to 14-membered heterocyclic group", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclic group includes single ring groups, fused ring groups and bridged groups. Examples of such heterocyclic groups include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahyrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane or thiazole.

Various embodiments of the invention are described herein. It will be recognized that features specified in each embodiment may be combined with other specified features to provide further embodiments.

In an embodiment of the invention as described anywhere herein, A is N.

In a further embodiment of the invention as described anywhere herein, $R^1$ is selected from H; $C_1$-$C_8$ alkyl optionally substituted by one or more halogen atoms; halogen; $C_6$-$C_{14}$ aryl; —($C_0$-$C_4$ alkyl)-3 to 14 membered heterocyclic group, wherein the heterocyclic group contains at least one heteroatom selected from N, O and S; and $NR^{11}R^{12}$, wherein the aryl and heterocyclic groups are each optionally substituted by one or more Z substituents.

In a yet further embodiment of the invention as described anywhere herein, $R^2$ is $C_1$-$C_8$ alkyl optionally substituted by one or more halogen atoms; $C_3$-$C_{10}$ cycloalkyl; or —$C_1$-$C_4$ alkyl-$C_3$-$C_8$ cycloalkyl. Suitably, $R^2$ is $CF_3$.

In a further embodiment of the invention as described anywhere herein, $R^3$ is H or methyl.

In a further embodiment of the invention as described anywhere herein, $R^a$ is H In a still further embodiment of the invention as described anywhere herein, E is $CR^7$.

An embodiment of the invention as defined above provides a compound according to Formula I, wherein
A is N
$R^1$ is selected from H; halogen; $C_6$-$C_{14}$ aryl; a 5 or 6-membered heterocyclic group, wherein the heterocyclic group contains at least one heteroatom selected from N, O and S; and $NR^{11}R^{12}$, wherein the aryl and heterocyclic groups are each optionally substituted by one or more Z substituents;
$R^2$ is $CF_3$;
$R^a$ is H;
$R^3$ is H or Me; and
E is $CR^7$, wherein all of the other variables are as defined anywhere herein.

In another embodiment individual compounds according to the invention are those listed in the Examples section below.

In another embodiment the invention provides a compound of the formula (I), which is selected from:
3-Amino-6-bromo-5-trifluoromethyl-pyrazine-2-carboxylic acid (5-trifluoromethyl-2H-pyrazol-3-yl)-amide;
3-Amino-6-bromo-5-trifluoromethyl-pyrazine-2-carboxylic acid (5-cyclopropyl-2H-pyrazol-3-yl)-amide;
3-Amino-6-bromo-5-trifluoromethyl-pyrazine-2-carboxylic acid (5-tert-butyl-2H-pyrazol-3-yl)-amide;
3-Amino-6-bromo-5-trifluoromethyl-pyrazine-2-carboxylic acid (5-methyl-2H-pyrazol-3-yl)-amide;
3-Amino-6-bromo-5-trifluoromethyl-pyridine-2-carboxylic acid (5-trifluoromethyl-2H-pyrazol-3-yl)-amide;
3-Amino-6-bromo-5-trifluoromethyl-pyrazine-2-carboxylic acid (2H-pyrazol-3-yl)-amide;
3-Amino-6-bromo-5-trifluoromethyl-pyridine-2-carboxylic acid (2H-pyrazol-3-yl)-amide;
3-Amino-6-pyrrolidin-1-yl-5-trifluoromethyl-pyrazine-2-carboxylic acid (5-trifluoromethyl-2H-pyrazol-3-yl)-amide;
3-Amino-6-morpholin-4-yl-5-trifluoromethyl-pyrazine-2-carboxylic acid (2H-pyrazol-3-yl)-amide;
3-Amino-5-trifluoromethyl-pyrazine-2-carboxylic acid (2H-pyrazol-3-yl)-amide;
5-[(3-Amino-6-bromo-5-trifluoromethyl-pyrazine-2-carbonyl)-amino]-1H-[1,2,4]triazole-3-carboxylic acid;
3-Amino-6-dimethylamino-5-trifluoromethyl-pyrazine-2-carboxylic acid (2H-pyrazol-3-yl)-amide;
3-Amino-6-bromo-5-trifluoromethyl-pyrazine-2-carboxylic acid (2H-[1,2,4]triazole-3-yl)amide;
3-Amino-6-chloro-5-trifluoromethyl-pyrazine-2-carboxylic acid (2H-pyrazole-3-yl)amide;
3-Amino-6-bromo-5-trifluoromethyl-pyrazine-2-carboxylic acid (5-piperidin-1-ylmethyl-2H-pyrazol-3yl)-amide;
3-Amino-6-bromo-N-(1H-pyrazolo[4,3-b]pyrazin-3-yl)-5-(trifluoromethyl)pyrazine-2-carboxamide;
tert-Butyl 3-(3-amino-6-bromo-5-(trifluoromethyl)pyrazine-2-carboxamido)-4,6-dihydropyrrolo[3,4-c]pyrazole-5(2H)-carboxylate;
3-Amino-6-bromo-N-(1H-pyrazolo[4,3-b]pyrazin-3-yl)-5-(trifluoromethyl)picolinamide;
3-Amino-6-bromo-N-(4-(pyridin-2-yl)-1H-pyrazol-5-yl)-5-(trifluoromethyl)pyrazine-2-carboxamide;
2-Amino-5-iodo-N-(1H-pyrazol-5-yl)-4-(trifluoromethyl) benzamide hydrochloride;
3-Amino-6-bromo-N-(1H-pyrazolo[3,4-b]pyridin-3-yl)-5-(trifluoromethyl)pyrazine-2-carboxamide;
3-Amino-6-chloro-N-(1H-pyrazol-5-yl)-5-(trifluoromethyl) picolinamide
Methyl 5-(3-amino-6-bromo-5-(trifluoromethyl)pyrazine-2-carboxamido)-1H-1,2,4-triazole-3-carboxylate;
3-Amino-N-(3-benzyl-1H-1,2,4-triazol-5-yl)-6-bromo-5-(trifluoromethyl)pyrazin-2-carboxamide;
3-Amino-6-(4-fluorophenyl)-N-(1H-pyrazol-3-yl)-5-(trifluoromethyl)picolinamide
3-Amino-6-(4-chloro-2-methyl-phenyl)-5-trifluoro methyl-pyridine-2-carboxylic acid (2H-pyrazol-3-yl)-amide;

5-Amino-2'-methoxy-3-trifluoro methyl-[2,3']bipyridinyl-6-carboxylic acid (1H-pyrazol-3-yl)-amide;
3-Amino-6-[3-(2-oxo-pyrrolidin-1-ylmethyl)-phenyl]-5-trifluoromethyl-pyridine-2-carboxylic acid (2H-pyrazol-3-yl)-amide;
5-Amino-6'-methoxy-3-trifluoromethyl-[2,3]bipyridinyl-6-carboxylic acid (2H-pyrazol-3-yl)-amide;
3-Amino-6-[4-(5-methyl-[1,3,4]oxadiazol-2-yl)-phenyl]-5-trifluoromethyl-pyridine-2-carboxylic acid (2H-pyrazol-3-yl)-amide;
3-Amino-5,6-bis-trifluoromethyl-pyrazine-2-carboxylic acid (4-methyl-2H-pyrazol-3-yl)-amide;
or a pharmaceutically acceptable salt or solvate thereof.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms.

Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

Some of the compounds of Formula I may exist in different tautomeric forms. Tautomerism is well known to those skilled in the art and the skilled person will readily appreciate which groups are able to tautomerise to form the different tautomeric forms. The invention includes all tautomeric forms of the compounds of Formula I. In particular, compounds of the invention may tautomerise in the following way:

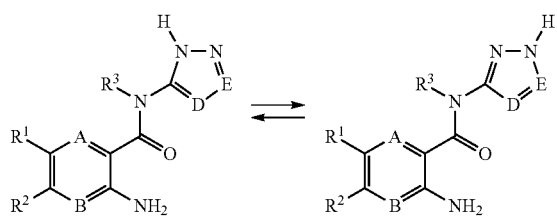

Both tautomeric forms are considered to be within the scope of the claims. Thus, reference to one specific tautomeric form is intended to include any and all alternative tautomeric forms.

The compounds of the invention may exist in both unsolvated and solvated forms. The term "solvate" is used herein to describe a molecular complex comprising the compound of the invention and one or more pharmaceutically acceptable solvent molecules, e.g., ethanol. The term "hydrate" is employed when said solvent is water.

Synthesis

The compounds of formula (I) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

Generally, compounds according to Formula I can be synthesized by the routes described in Scheme 1 and the Examples.

When A is nitrogen and B is CH, the pyridinyl moiety may be synthesised according to the general scheme 1 shown below.

Scheme 1

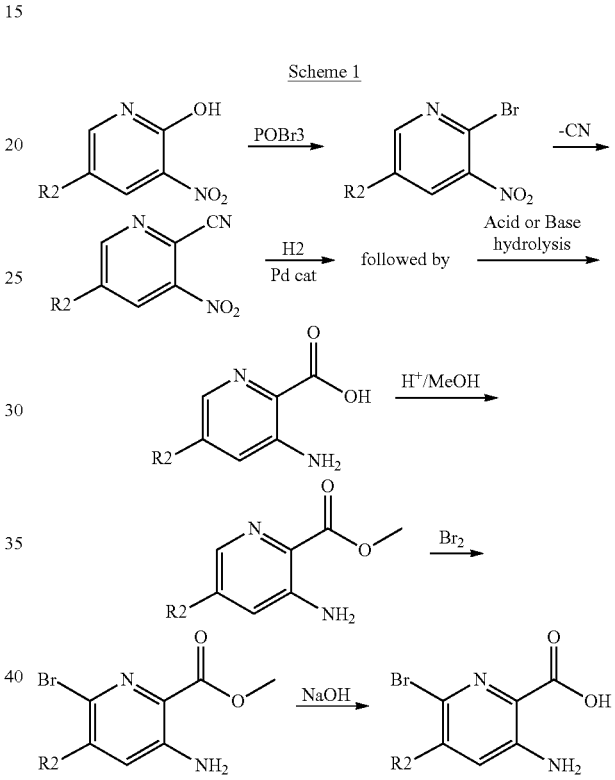

A similar synthetic process may be used for compounds according to the invention in which A is CH and B is nitrogen by use of the relevant starting compound.

When A and B are both nitrogen, the pyrazine moiety may be synthesised according to the general scheme 2 shown below.

Scheme 2

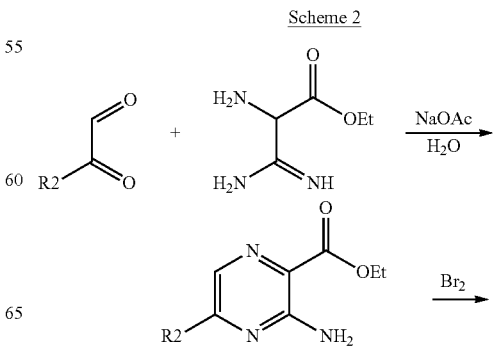

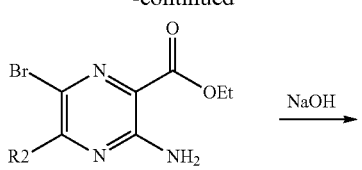

When A and B are both CH, the phenyl moiety may be synthesised according to the general scheme 3 shown below.

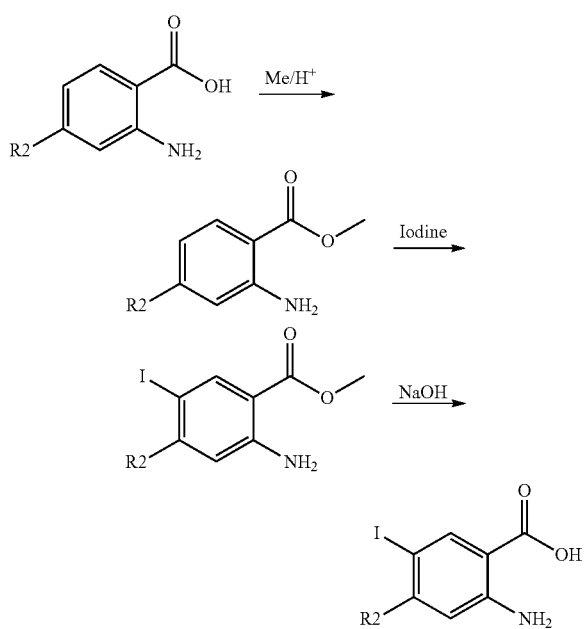

The pyrazole or triazole moiety is typically added via an amide formation reaction as shown below in general scheme 4

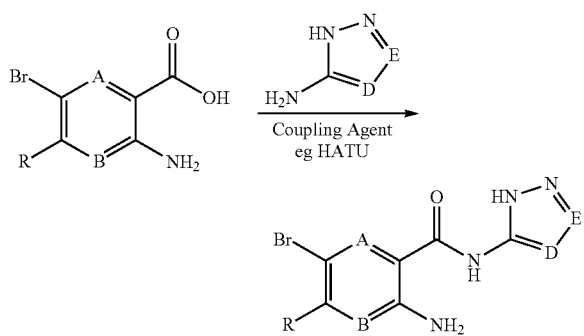

The $R^1$ group may be introduced via a palladium catalysed cross-coupling reaction as shown in general scheme 5 below, or by an aromatic nucleophilic substitution reaction as shown in general scheme 6 below.

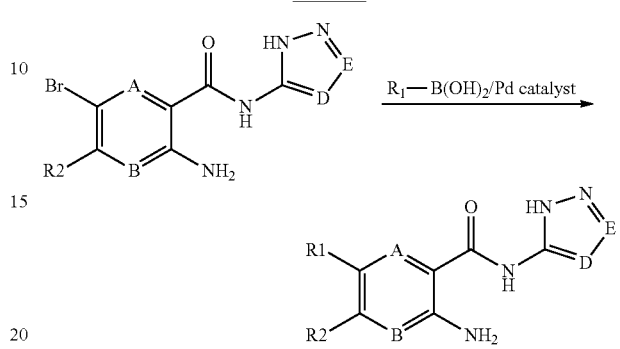

In the above general schemes, A, B, D, E, $R^1$ and $R^2$ are all as defined anywhere herein.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

The skilled person will appreciate that the general synthetic routes detailed above show common reactions to transform the starting materials as required. The specific reaction conditions are not provided, but these are well known to those skilled in the art and appropriate conditions considered to be within the skilled person's common general knowledge.

The starting materials are either commercially available compounds or are known compounds and can be prepared from procedures described in the organic chemistry art.

Compounds of formula (I), in free form, may be converted into salt form, and vice versa, in a conventional manners understood by those skilled in the art. The compounds in free or salt form can be obtained in the form of hydrates or solvates containing a solvent used for crystallisation. Compounds of formula (I) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of formula I in free form or in salt form, exhibit valuable pharmacological properties, e.g. CFTR modulating properties, e.g. as indicated in vitro and in vivo tests as provided in the next sections and are therefore indicated for therapy.

Having regard to their modulation of CFTR activity, compounds of formula (I), in free or pharmaceutically acceptable salt form are useful in the treatment of conditions which respond to the modulation of CFTR activity, particularly conditions benefiting from mucosal hydration such as cystic fibrosis.

A further aspect of the invention provides a compound of Formula I as defined anywhere herein for use as a medicament.

A further aspect of the invention provides a compound of Formula I for use in the treatment of a disease or disorder mediated by CFTR, in particular an inflammatory or allergic condition, particularly an inflammatory or obstructive airways disease or mucosal hydration. Such conditions include, for example, cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

A still further aspect of the present invention provides for the use of a compound of formula (I), as defined in any of the aforementioned embodiments, in free or pharmaceutically acceptable salt form, for the manufacture of a medicament for the treatment of a disease or disorder mediated by CFTR, in particular an inflammatory or allergic condition, particularly an inflammatory or obstructive airways disease or mucosal hydration.

An embodiment of the present invention provides for the use of a compound of formula (I), as defined in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

In another aspect, the invention provides a method of treating a disease or disorder which is treated by modulation of CFTR comprising administration of a therapeutically acceptable amount of a compound of formula (I). In one embodiment, the disease or disorder is an inflammatory or allergic condition, particularly an inflammatory or obstructive airways disease or mucosal hydration. Such conditions include, for example, cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

Diseases mediated by modulation of CFTR activity, include diseases associated with the regulation of fluid volumes across epithelial membranes. For example, the volume of airway surface liquid is a key regulator of mucociliary clearance and the maintenance of lung health. The modulation of CFTR activity will promote fluid accumulation on the mucosal side of the airway epithelium thereby promoting mucus clearance and preventing the accumulation of mucus and sputum in respiratory tissues (including lung airways).

Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by modulation of CFTR activity also include diseases other than respiratory diseases that are associated with abnormal fluid regulation across an epithelium, perhaps involving abnormal physiology of the protective surface liquids on their surface, e.g., Sjögren's Syndrome, xerostomia (dry mouth) or keratoconjunctivitis sire (dry eye). Furthermore, modulation of CFTR activity in the kidney could be used to promote diuresis and thereby induce a hypotensive effect.

Treatment in accordance with the invention may be symptomatic or prophylactic.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

Dry eye disease is characterized by a decrease in tear aqueous production and abnormal tear film lipid, protein and mucin profiles. There are many causes of dry eye, some of which include age, laser eye surgery, arthritis, medications, chemical/thermal burns, allergies and diseases, such as cystic fibrosis and Sjögren's Syndrome. Increasing anion secretion via CFTR would enhance fluid transport from the corneal endothelial cells and secretory glands surrounding the eye to increase corneal hydration. This would help to alleviate the symptoms associated with dry eye disease.

Sjögren's Syndrome is an autoimmune disease in which the immune system attacks moisture-producing glands throughout the body, including eye, mouth, skin, respiratory tissue, liver, vagina and gut. Symptoms include dry eye, dry mouth and dry vagina, as well as lung disease. The disease is also associated rheumatoid arthritis, systemic lupus, systemic sclerosis and polymypositis/dermatomyositis. Defective protein trafficking is believed to cause the disease, for which treatment options are limited. Modulators of CFTR activity may hydrate the various organs affected by the disease and help to alleviate the associated symptoms.

In accordance with the foregoing, the invention also provides as a further aspect a method for the treatment of a condition responsive to modulation of CFTR activity, e.g., diseases associated with the regulation of fluid volumes across epithelial membranes, particularly an obstructive airways disease, which comprises administering to a subject, particularly a human subject, in need thereof a compound of formula (I), in free form or in the form of a pharmaceutically acceptable salt.

In another aspect the invention provides a compound of formula (I), in free form or in the form of a pharmaceutically acceptable salt, for use in the treatment of a condition responsive to modulation of CFTR activity, e.g., diseases associated with the regulation of fluid volumes across epithelial membranes, particularly an obstructive airways disease, e.g., cystic fibrosis and COPD.

In another aspect the invention provides a compound of formula (I), in free form or in the form of a pharmaceutically acceptable salt, for use in the manufacture of a medicament for the treatment of a condition responsive to modulation of CFTR activity, e.g., diseases associated with the regulation of fluid volumes across epithelial membranes, particularly an obstructive airways disease, e.g., cystic fibrosis and COPD.

The suitability of CFTR activity modulators as a treatment of a disease benefiting from mucosal hydration, may be tested by determining the movement of chloride ions in a suitable cell-based assay. For example single cells or confluent epithelia, endogenously expressing or engineered to overexpress CFTR can be used to assess channel function using electrophysiological techniques or ion flux studies. See methods described in: Hirsh et al., *J Pharm Exp Ther* (2004); Moody et al., *Am J Physiol Cell Physiol* (2005).

CFTR activity modulators, including the compounds of formula (I), are also useful as co-therapeutic agents for use in combination with other drug substances, such as anti-inflammatory, bronchodilatory, antihistamine or anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by CFTR. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by CFTR wherein the medicament is prepared for administration with another therapeutic agent. The invention also provides the use of another therapeutic agent for treating a disease or condition mediated by CFTR, wherein the medicament is administered with a compound of formula (I).

The invention also provides a compound of formula (I) for use in a method of treating a disease or condition mediated by CFTR, wherein the compound of formula (I) is prepared for administration with another therapeutic agent. The invention also provides another therapeutic agent for use in a method of treating a disease or condition mediated by CFTR, wherein the other therapeutic agent is prepared for administration with a compound of formula (I). The invention also provides a compound of formula (I) for use in a method of treating a disease or condition mediated by CFTR, wherein the compound of formula (I) is administered with another therapeutic agent. The invention also provides another therapeutic agent for use in a method of treating a disease or condition mediated by CFTR, wherein the other therapeutic agent is administered with a compound of formula (I).

The invention also provides the use of a compound of formula (I) for treating a disease or condition mediated by CFTR, wherein the patient has previously (e.g. within 24 hours) been treated with another therapeutic agent. The invention also provides the use of another therapeutic agent for treating a disease or condition mediated by CFTR, wherein the patient has previously (e.g. within 24 hours) been treated with a compound of formula (I).

Accordingly, the invention includes as a further aspect a combination of a CFTR activity modulator with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the CFTR activity modulator and the further drug substance may be in the same or different pharmaceutical composition.

Suitable antibiotics include macrolide antibiotics, e.g., tobramycin (TOBI™).

Suitable DNase drug substances include dornase alfa (Pulmozymen™), a highly-purified solution of recombinant human deoxyribonuclease I (rhDNase), which selectively cleaves DNA. Dornase alfa is used to treat cystic fibrosis.

Other useful combinations of CFTR activity modulators with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266; WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 00/75114, which document is incorporated herein by reference, preferably compounds of the Examples thereof, especially a compound of formula:

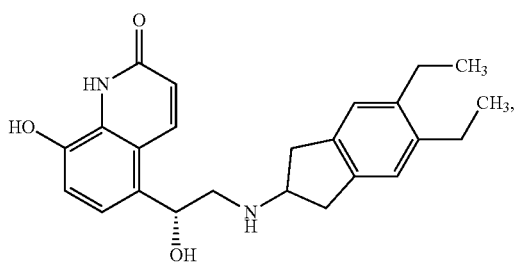 [SMILES: CCc1cc2c(cc1CC)CC(NC[C@H](O)c1ccc(O)c3[nH]c(=O)ccc13)C2]

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

The invention includes as a further aspect a combination of a CFTR activity modulator with a CFTR corrector, wherein the CFTR activity modulator and the CFTR corrector may be in the same or different pharmaceutical composition. Suitable CFTR correctors include VX-809

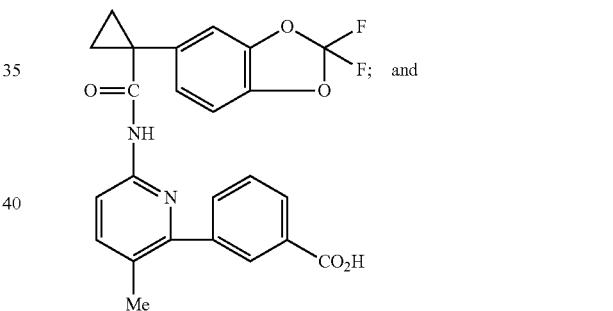

VX-661

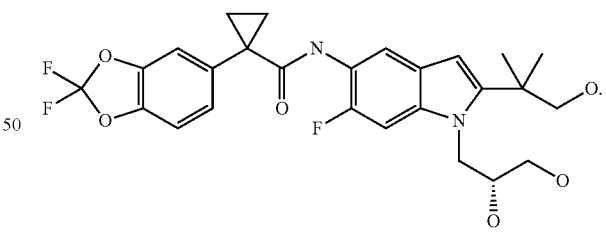

In another aspect, the present invention provides a pharmaceutical composition comprising a compound of the present invention and a pharmaceutically acceptable carrier.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

Further aspects of the invention include:
(a) a compound of formula (I) in inhalable form, e.g., in an aerosol or other atomisable composition or in inhalable particulate, e.g., micronised form;

(b) an inhalable medicament comprising a compound of formula (I) in inhalable form;
(c) a pharmaceutical product comprising a compound of formula (I) in inhalable form in association with an inhalation device; and
(d) an inhalation device containing a compound of formula I in inhalable form.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. In general, suitable daily dosages for administration by inhalation are of the order of 0.005-10 mg, while for oral administration suitable daily doses are of the order of 0.05-100 mg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by CFTR, or (ii) associated with CFTR activity, or (iii) characterized by activity (normal or abnormal) of CFTR; or (2) reducing or inhibiting the activity of CFTR; or (3) reducing or inhibiting the expression of CFTR. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CFTR; or at least partially reducing or inhibiting the expression of CFTR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Pharmaceutical Use and Assay

Compounds of formula (I) and their pharmaceutically acceptable salts, hereinafter referred to alternatively as "agents of the invention", are useful as pharmaceuticals. In particular, the compounds are suitable CFTR activity modulators and may be tested in the following assays.

Membrane Potential Assay

CFTR activity can be quantified by measuring the transmembrane potential. The means for measuring the transmembrane potential in a biological system can employ a number of methods including electrophysiological and optical fluorescence-based membrane potential assays.

The optical membrane potential assay utilises a negatively charged potentiometric dye, such as the FLIPR membrane potential dye (FMP) (see Baxter D F, Kirk M, Garcia A F, Raimondi A, Holmqvist M H, Flint K K, Bojanic D, Distefano P S, Curtis R, Xie Y. 'A novel membrane potential-sensitive fluorescent dye improves cell-based assays for ion channels.' J Biomol Screen. 2002 Feb.; 7(1):79-85) which when extraceullar is bound to a quenching agent. Upon cellular depolarisation the negatively charged dye redistributes to the intracellular compartment, unbinding from the membrane impermeant quench agent, yielding an increase in fluorescence. This change in fluoresence is proportional to the change in transmembrane potential which can result from the activity of CFTR. The changes in fluorescence can be monitored in real time by an appropriately equipped fluorescence detector such as the FLIPR (fluorometric imaging plate reader) in 96 or 384-well microtitre plates.

Cell Culture:

Chinese hamster ovary (CHO) cells stably expressing the ΔF508-CFTR channel were used for membrane potential experiments. Cells were maintained at 37° C. in 5% v/v $CO_2$ at 100% humidity in Modified Eagles medium (MEM) supplemenetd with 8% v/v foetal calf serum, 100 μg/ml methotrexate and 100 U/ml penicillin/streptomycin. Cells were grown in 225 cm² tissue culture flasks. For membrane potential assays cells were seeded into 96 well plates at 40,000 cells per well, allowed to adhere and then maintained at 26° C. for 48 h to facilitate channel insertion.

Potentiator Assay:

The membrane potential screening assay utilised a low chloride ion containing extraceullular solution (~5 mM) combined with a double addition protocol. The first addition was of buffer with or without test compound followed 5 minutes later by an addition of forskolin (1-20 μM)—this protocol favours maximum chloride efflux in response to ΔF508-CFTR activation. The ΔF508-CFTR mediated chloride ion efflux leads to a membrane depolarisation which is optically monitoried by the FMP dye.

Solutions:

Low chloride extracellular (mM): 120 Na-gluconate, 1.2 $CaCl_2$, 3.3 $KH_2PO_4$, 0.8 $K_2HPO_4$, 1.2 $MgCl_2$, 10.0 D-glucose, 20.0 HEPES, pH 7.4 with NaOH FMP dye: made up as per manufacuturers instructions in low chloride extracellular solution detailed above, at 10× final concentration, and stored as 1 mL aliquots at −20° C.

IonWorks Quattro Assay:

CFTR activity can also be quantified electrophysiologically using the whole-cell configuration of the patch clamp technique (Hamill et al Pflugers Acrhive 1981). This assay directly measures the currents associated with chloride flow through CFTR channels whilst either maintaining or adjusting the transmembrane voltage. This assay can use either single glass micropipettes or parallel planar arrays to measure CFTR activity from native or recombinant cell systems. Currents measured using parallel planar arrays can be quantified using an appropriately equipped instrument such as the IonWorks Quattro (Molecular Devices) or the Qpatch (Sophion). The Quattro system can measure CFTR currents from either a single cell per recording well (HT configuration) or alternatively from a population of 64 cells per well (Population Patch Clamp PPC) (Finkel A, Wittel A, Yang N, Handran S, Hughes J, Costantin J. 'Population patch clamp improves data consistency and success rates in the measurement of ionic currents.' J Biomol Screen. 2006 Aug.; 11(5):488-96).

Cell Culture:

Chinese hamster ovary (CHO) cells stably expressing the ΔF508-CFTR channel were used for IonWorks Quattro experiments. Cells were maintained at 37° C. in 5% v/v $CO_2$ at 100% humidity in D-MEM supplemented with 10% (v/v) FCS, 100 U/mL Penicillin/Streptomycin, 1% (v/v) NEAA, 1 mg/ml Zeocin and 500 ug/ml Hygromycin B. For experiments cells were grown in 225 cm² tissue culture flasks until near confluence and then cultured at 26° C. for 48-72 h to facilitate channel insertion. Cells were removed from the flask and resuspended in either extracellular recording solution for immediate experimentation or alternatively in growth medium supplemented with 10% v/v DMSO and frozen to −80° C. as 1-2 mL aliquots for use at a later date.

Potentiator Assay:

Cells, at a density of 1.5-3 million per mL, were placed on the Quattro system, added to the planar patch array and seals allowed to establish for 5-10 mins. After assessing seal resistances (commonly >50 MΩ), whole-cell access was obtained by perforation with 100 μg/mL amphotericin B. Baseline currents were measured by a pre-compound scan obtained by application of a voltage ramp from −100 to +100 mV. This was followed by addition of either buffer or test compound diluted in the extracellular solution supplemented with 20 μM forskolin, to each of the 384 wells of the planar parch array. After an incubation step (5-20 minutes) the post-compound currents were measured again by application of a voltage ramp from −100 to +100 mV. The difference in currents between the pre- and post-compound scans defined the efficacy of CFTR potentiation.

Solutions:

Extracellular solution (ECS): 145 mM NaCl, 4 mM CsCl, 5 mM D-glucose, 10 mM TES, 1 mM $CaCl_2$, 1 mM $MgCl_2$, pH 7.4 NaOH Intracellular buffer (ICS): 113 mM L-Aspartic acid, 113 mM CsOH, 27 mM CsCl, 1 mM NaCl, 1 mM $MgCl_2$, 1 mM EGTA, 10 mM TES. pH 7.2 with CsOH. Filter sterilized before use.

Ion Transport Assay:

Another method to measure CFTR function is Ussings chamber short circuit current measurement. Engineered or native epithelial cells are grown to confluent monolayer on a semi-permeable filter and sandwiched between two perspex blocks. The flow of chloride ions via CFTR from one side of the epithelia to the other can be quantified by measuring the flow of current whilst maintaining the transepithelial potential at 0 mV. This is achieved using KCl filled agar-based electrodes to both clamp the cellular monolayer and measure the flow of currents.

Cell Culture:

FRT cells stably expressing ΔF508-CFTR were cultured on plastic in Coon's modified F-12 medium supplemented with 32 mM $NaHCO_3$, 10% v/v fetal bovine serum, 2 mM L-glutamine, 100 U/mL penicillin, 100 μg/mL streptomycin and 30 μg/mL hygromycin B as the growth medium. For Ussing chamber experiments, the cells were grown as polarized epithelia on Snapwell permeable support inserts (500000 cells/insert in growth medium) and cultured for 7 to 9 days. The inserts were fed with fresh Coon's modified F-12 growth medium every 48 hours, and 24 hours prior to Ussing chamber experiment. To increase the ΔF508 CFTR protein expression at the cell surface, plates were incubated at 27° C. for 48 h before performing an Ussing chamber experiment.

Potentiator Assay:

Fischer Rat Thyroid (FRT) epithelial cells, stably expressing human ΔF508-CFTR were used as monolayer cultures on permeable supports. Cl⁻ current was measured using the short circuit current technique, under an imposed basolateral to apical Cl⁻ gradient in Ussing chambers. To measure stable Cl⁻ currents, FRT cells were cultured for 48 h at 27° C. to facilitate the insertion of ΔF508 CFTR into the plasma membrane. Ussing chamber studies were likewise conducted at 27° C. Under these conditions, the effects of cumulative additions of test compounds on ΔF508 CFTR currents could be quantitated with both potency and efficacy endpoints. Compounds were added to both the apical and basloalteral sides subsequent to addition of 10 μM forskolin. Efficacy of compounds was compared to a known potentiator such as gensitein.

Solutions:

Basolateral Ringer solution (mM): 126 NaCl, 24 $NaHCO_3$, 0.38 $KH_2PO_4$, 2.13 $K_2HPO_4$, 1 $MgSO_4$, 1 $CaCl_2$ and 10 glucose.

Apical Ringer solution (mM): 140 Na-gluconate, 1 $MgSO_4$, 2 $CaCl_2$, 1 HCl, 10 glucose and 24 $NaHCO_3$.

Compounds can also be tested for their ability to stimulate insertion of £F508 CFTR into the cell membrane using the above assays. For these assays the protocols were identical other than cells were not cultured at low temperature (26 or 27° C.) but instead incubated with test compounds for 12-24 h prior to assay.

Compounds of the Examples, herein below, generally have Ki values in the data measurements described above below 10 μM. For example, the following Example compounds have the specified Ki values: Example 5: 0.07 μM, Example 7: 0.01 μM, Example 14: 0.255 μM, Example 18: 0.004 μM, Example 19: 1.55 μM, Example 22: 0.025 μM, Example 24: 0.02 μM, Example 25.1: 3.8 nM, Example 25.2: 13 nM, Example 25.3: 14 nM, Example 26.1: 30 nM, Example 26.2: 45 nM: Example 26.3: 0.160 μM and Example 27: 19 nM.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The invention is illustrated by the following Examples.

EXAMPLES

General Conditions

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H]$^+$ refers to mono-isotopic molecular weights.

NMR spectra were run on open access Bruker AVANCE 400 NMR spectrometers using ICON-NMR. Spectra were measured at 298K and were referenced using the solvent peak.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

ABBREVIATIONS app apparent
ATP adenosine 5'-triphosphate
BINAP racemic 2,2'-bis(diphenylphosphino)-1,1'-binaphthyl
9-BBN 9-Borabicyclo[3.3.1]nonane
BOC tertiary butyl carboxy
br broad
BSA bovine serum albumin
d doublet
dd doublet of doublets
DCM dichloromethane
DIEA diethylisopropylamine
DIPEA diisopropylethylamine
DMF N,N-dimethylformamide
DMSO dimethylsulfoxide
DTT dithiothreitol
EDTA ethylenediamine tetraacetic acid
ESI electrospray ionization
EDCI 1-ethyl-3-(3'-dimethylaminopropyl) carbodiimide
EtOAc ethyl acetate
FCC flash column chromatography
h hour(s)
HATU 2-(7-Aza-1H-benzotriazole-1-yl)-1,1,3,3-tetramethyluronium hexafluorophosphate
HBTU 1-[bis(dimethylamino)methylene]-1H-benzotriazoliumhexafluorophosphate(1-) 3-oxide
HOBt 1-hydroxy-7-azabenzotriazole
HPLC high pressure liquid chromatography
IR infrared spectroscopy
LCMS liquid chromatography and mass spectrometry
MeOH methanol
MEMCl 2-methoxyethoxymethyl chloride
MS mass spectrometry
MW microwave
m multiplet
min minutes
ml milliliter(s)
m/z mass to charge ratio
NMR nuclear magnetic resonance
ppm parts per million
PyBOP benzotriazol-1-yloxytripyrrolidinophosphonium hexafluorophosphate
PS polymer supported
PPTS Pyridinium para-toluenesulfonate
PEAX PE-anion exchange (e.g. Isolute® PE-AX columns from Biotage)
rac racemic
RT room temperature
s singlet
SCX-2 strong cation exchange (e.g. Isolute® SCX-2 columns from Biotage)
t triplet
TEA triethylamine
TFA trifluoroacetic acid
THF tetrahydrofuran
Tris.HCl aminotris(hydroxymethyl)methane hydrochloride Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:

| Method 2minLC__v002 | |
|---|---|
| Column | Waters BEH C18 50 × 2.1 mm, 1.7 μm |
| Column Temperature | 50° C. |
| Eluents | A: H$_2$O, B: methanol, both containing 0.1% TFA |
| Flow Rate | 0.8 ml/min |
| Gradient | 0.20 min 5% B; 5% to 95% B in 1.30 min, 0.25 min 95% B |

| Method 2minLC__v003 | |
|---|---|
| Column | Waters BEH C18 50 × 2.1 mm, 1.7 μm |
| Column Temperature | 50° C. |
| Eluents | A: H$_2$O, B: acetonitrile, both containing 0.1% TFA |
| Flow Rate | 0.8 ml/min |
| Gradient | 0.20 min 5% B; 5% to 95% B in 1.30 min, 0.25 min 95% B |

Preparation of Final Compounds

Especially preferred compounds of the present invention include those shown in Table 1 below, the methods of preparation being described hereinafter.

TABLE 1

| Ex. | Structure | [M + H]+ | 1H NMR |
|---|---|---|---|
| 1 | 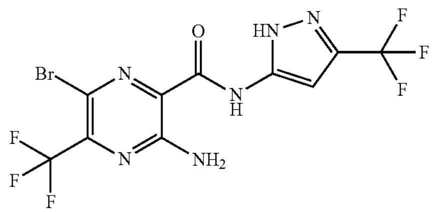 [SMILES: Nc1nc(C(F)(F)F)c(Br)nc1C(=O)Nc1cc(C(F)(F)F)n[nH]1] | 419 | (400 MHz, DMSO - d6) δ 13.2 (1H, s), 11.3 (1H, s), 8.15 (2H, broad), 6.7 (1H, s). |
| 2 | 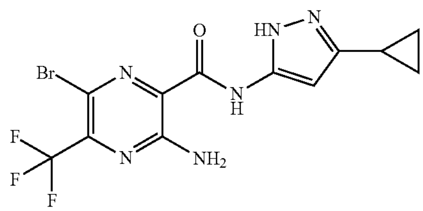 [SMILES: Nc1nc(C(F)(F)F)c(Br)nc1C(=O)Nc1cc(C2CC2)n[nH]1] | 391 | (400 MHz, DMSO - d6) δ 12.35 (1H, s), 10.2 (1H, s), 8.1 (2H, broad s), 6.3 (1H, s), 1.9 (1H, m), 0.95 (2H, m), 0.7 (2H, m). |
| 3 | 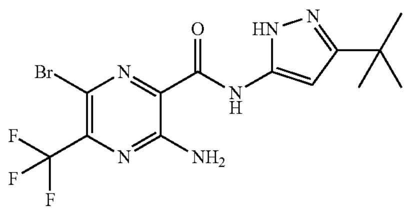 [SMILES: CC(C)(C)c1cc(NC(=O)c2nc(Br)c(C(F)(F)F)nc2N)[nH]n1] | 407 | (400 MHz, DMSO - d6) δ 12.3 (1H, s), 10.25 1H, s), 8.1 (2H, s), 6.42 (1H, s), 1.3 (9H, s). |
| 4 | 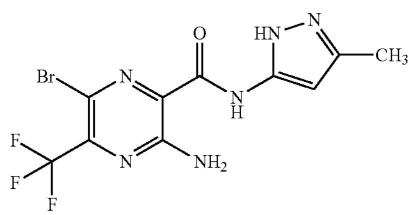 [SMILES: Cc1cc(NC(=O)c2nc(Br)c(C(F)(F)F)nc2N)[nH]n1] | 365 | (400 MHz, DMSO - d6) δ 12.3 (1H, s), 10.26 (1H, s), 8.1 (2H, s), 6.38 (1H, s), 2.7 (3H, s). |
| 5 | 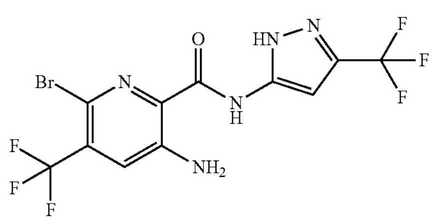 [SMILES: Nc1cc(C(F)(F)F)c(Br)nc1C(=O)Nc1cc(C(F)(F)F)n[nH]1] | 418 | (400 MHz, DMSO - d6) δ 13.2 (1H, s), 11.04 (1H, s), 7.8 (1H, s), 7.38 (2H, s), 6.72 (1H, s). |
| 6 | 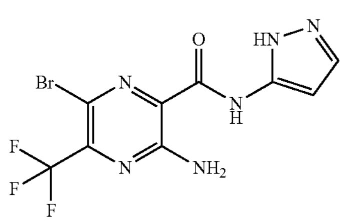 [SMILES: Nc1nc(C(F)(F)F)c(Br)nc1C(=O)Nc1ccn[nH]1] | 351 | (400 MHz, DMSO - d6) δ 12.6 (1H, s), 10.32 (1H, s), 8.08 (2H, broad s), 7.72 (1H, s), 6.62 (1H, s) |
| 7 | 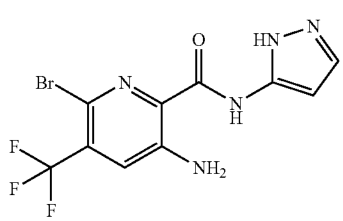 [SMILES: Nc1cc(C(F)(F)F)c(Br)nc1C(=O)Nc1ccn[nH]1] | 350 | (400 MHz, DMSO - d6) δ 12.6 (1H, s), 10.06 (1H, s), 7.78 (1H, s), 7.7 (1H, s), 7.32 (2H, s), 6.62 (1H, s) |

TABLE 1-continued

| Ex. | Structure | [M + H]⁺ | ¹H NMR |
|---|---|---|---|
| 8 | 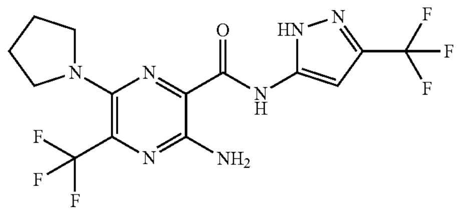 [SMILES: Nc1nc(C(F)(F)F)c(N2CCCC2)nc1C(=O)Nc1cc(C(F)(F)F)n[nH]1] | 410 | (400 MHz, DMSO - d6) δ 13.5 (1H, s), 10.6 (1H, s), 7.1 (2H, s), 6.7 (1H, s), 3.5 (4H, m), 1.9 (4H, m). |
| 9 | 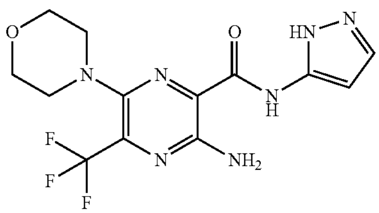 [SMILES: Nc1nc(C(F)(F)F)c(N2CCOCC2)nc1C(=O)Nc1ccn[nH]1] | 358 | (400 MHz, DMSO - d6) δ 12.6 (1H, s), 10.36 (1H, s), 7.75 (1H, s), 7.68 (2H, s), 6.65 (1H, s), 3.75 (4H, m), 3.06 (4H, m). |
| 10 | 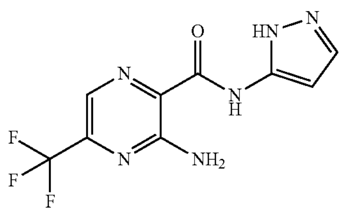 [SMILES: Nc1nc(C(F)(F)F)cnc1C(=O)Nc1ccn[nH]1] | 273 | (400 MHz, DMSO - d6) δ 12.56 (1H, s), 10.4 (1H, s), 8.3 (1H, s), 8.05 (2H, s), 7.74 (1H, s), 6.64 (1H, s) |
| 11 | 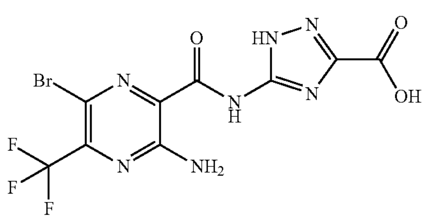 [SMILES: Nc1nc(C(F)(F)F)c(Br)nc1C(=O)Nc1nc(C(=O)O)n[nH]1] | 396 | (400 MHz, DMSO - d6) δ 14.2 (1H, s), 13.2 (1H, s), 12.06 (1H, s), 8.0 (2H, broad s). |
| 12 | 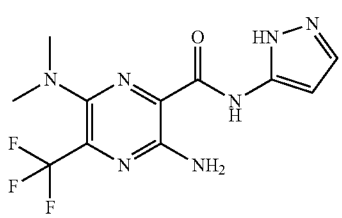 [SMILES: CN(C)c1nc(C(=O)Nc2ccn[nH]2)c(N)nc1C(F)(F)F] | 316 | (400 MHz, DMSO - d6) δ 12.5 (1H, s), 10.2 (1H, s), 7.72 (1H, s), 7.5 (2H, s), 6.64 (1H, s), 2.8 (6H, s). |
| 13 | 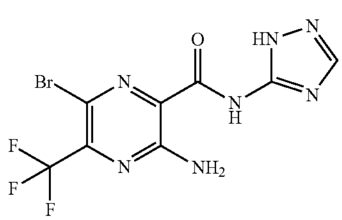 [SMILES: Nc1nc(C(F)(F)F)c(Br)nc1C(=O)Nc1ncn[nH]1] | 352 | (400 MHz, DMSO - d6) δ 13.7 (1H, broad hump), 11-12 (1H, broad hump), 8.2 (3H, broad peak) |
| 14 | 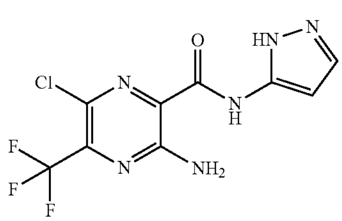 [SMILES: Nc1nc(C(F)(F)F)c(Cl)nc1C(=O)Nc1ccn[nH]1] | 307 | (400 MHz, DMSO - d6) δ 12.6 (1H, s), 10.4 (1H, s), 8.1 (2H, s), 7.7 (1H, s), 6.6 (1H, s). |

TABLE 1-continued

| Ex. | Structure | [M + H]+ | 1H NMR |
|---|---|---|---|
| 15 | 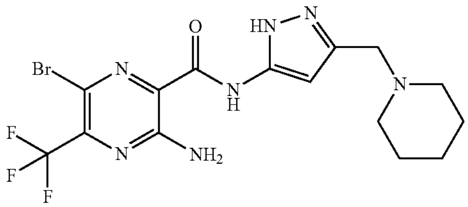 [SMILES: Nc1nc(C(F)(F)F)c(Br)nc1C(=O)Nc1cc(CN2CCCCC2)n[nH]1] | 448 | (400 MHz, DMSO - d6) δ 12.5 (1H, s), 10.3 (1H, s), 8.08 (2H, s), 5.16 (1H, s), 3.48 (2H, m), 2.35 (4H, m), 1.50 (4H, m), 1.36 (2H, m) |
| 16 | 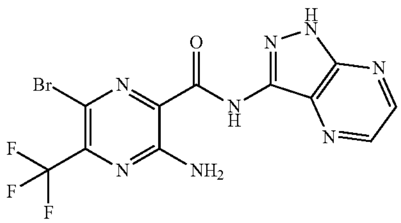 [SMILES: Nc1nc(C(F)(F)F)c(Br)nc1C(=O)Nc1n[nH]c2nccnc12] | 403 | (400 MHz, DMSO - d6) δ 14.0 (1H, s), 10.90 (1H, s), 8.65 (2H, dd), 8.09 (2H, br s). |
| 17 | 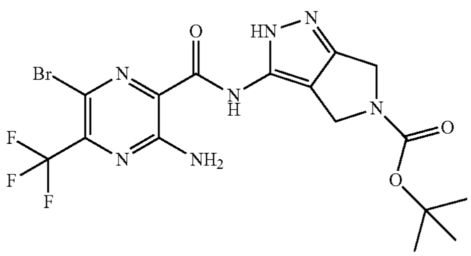 [SMILES: CC(C)(C)OC(=O)N1Cc2n[nH]c(NC(=O)c3nc(Br)c(C(F)(F)F)nc3N)c2C1] | 494 | (400 MHz, DMSO - d6) δ 12.55 (0.5H, d), 12.10 (0.5H, d), 11.05 (0.5H, br s), 10.49 (0.5H, br s), 8.04 (2H, m), 4.49 (2H, d), 4.45 (1H, d), 4.30 (1H, d), 1.46 (9H, s). |
| 18 | 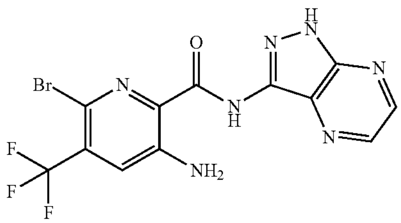 [SMILES: Nc1cc(C(F)(F)F)c(Br)nc1C(=O)Nc1n[nH]c2nccnc12] | 402 | (400 MHz, DMSO - d6) δ 13.92 (1H, s), 10.60 (1H, s), 8.63 (2H, dd), 7.80 (1H, s), 7.32 (2H, br s). |
| 19 | 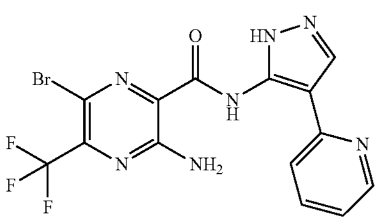 [SMILES: Nc1nc(C(F)(F)F)c(Br)nc1C(=O)Nc1[nH]ncc1-c1ccccn1] | 430 | (400 MHz, DMSO - d6) δ 13.50 (0.5H, s), 13,30 (0.5H, s), 13.18 (0.5H, s), 12.80 (0.5H, s), 8.74 (0.5H, m), 8.69 (0.5H, m), 8.50 (0.5H, s), 8.21 (2H, s), 8.16 (0.5H, s), 7.86 (1H, m), 7.81 (1H, d), 7.25 (1H, m). |
| 20 | 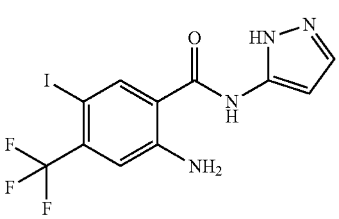 [SMILES: Nc1cc(C(F)(F)F)c(I)cc1C(=O)Nc1ccn[nH]1] | 397 | (400 MHz, DMSO - d6) δ 10.89 (1H, br s), 8.25 (1H, s), 7.65 (1H, d), 7.56-5.74 (3H, br hump), 7.22 (1H, s), 6.57 (1H, d) |
| 21 | 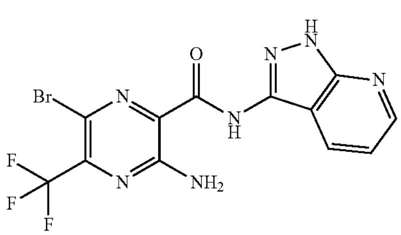 [SMILES: Nc1nc(C(F)(F)F)c(Br)nc1C(=O)Nc1n[nH]c2ncccc12] | 402 | (400 MHz, DMSO - d6) δ 13.48 (1H, s), 10.95 (1H, s), 8.54 (1H, dd), 8.37 (1H, dd) 8.10 (2H, br s), 7.21 (1H, dd) |

TABLE 1-continued

| Ex. | Structure | [M + H]+ | 1H NMR |
|---|---|---|---|
| 22 | 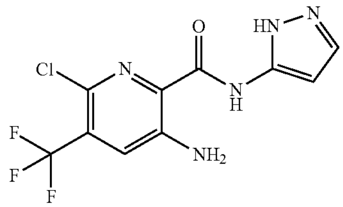 [SMILES: Nc1cc(C(F)(F)F)c(Cl)nc1C(=O)Nc1ccn[nH]1] | 306 | (400 MHz, DMSO - d6) δ 12.56 (1H, s), 10.05 (1H, s), 7.08 (1H, s), 7.70 (1H, s), 7.33 (2H, br s), 6.62 (1H, s) |
| 23 | 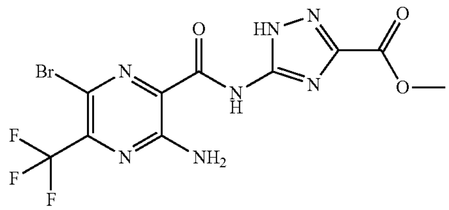 [SMILES: COC(=O)c1n[nH]c(NC(=O)c2nc(Br)c(C(F)(F)F)nc2N)n1] | 410 | (400 MHz, DMSO - d6) δ 14.3 (1H, s), 12.1 (1H, s), 8.05 (2H, s), 3.85 (3H, s) |
| 24 | 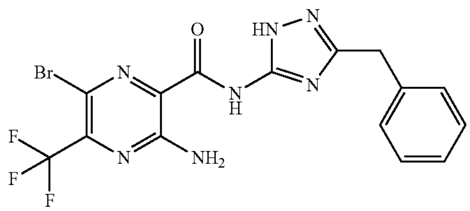 [SMILES: Nc1nc(C(F)(F)F)c(Br)nc1C(=O)Nc1nc(Cc2ccccc2)n[nH]1] | 442 | (400 MHz, DMSO - d6) δ 13.7 (1H, s), 13.45 (1H, s), 11.65 (1H, s), 10.5 (1H, s), 8.05 (2H, s), 7.3 (5H, m), 4.05 (1H, s), 3.95 (1H, s). |

Example 1

3-Amino-6-bromo-5-trifluoromethyl-pyrazine-2-carboxylic acid (5-trifluoromethyl-2H-pyrazol-3-yl)-amide To a stirred solution of 3-amino-6-bromo-5-trifluoromethyl-pyrazine-2-carboxylic acid (Intermediate 2) (100 mg, 0.350 mmol) in dry NMP (2 ml) was added NEt$_3$ (0.097 ml, 0.699 mmol) followed by 3-(trifluoromethyl)-1H-pyrazol-5-amine (48.0 mg, 0.318 mmol). The mixture was stirred at RT for 5 minutes, before treating with HATU (133 mg, 0.350 mmol). The resulting orange solution was stirred at RT for 10 minutes and then partitioned between EtOAc (50 ml) and 1M NaOH (30 ml). The organic portion was separated and washed with 1M NaOH (20 ml), water (20 ml), dried (MgSO$_4$) and concentrated in vacuo. Purification of the crude residue by chromatography on silica eluting with iso-hexane/EtOAc (gradient of 0 to 50% EtOAc) afforded the title compound as a yellow solid.

Examples 2-7

These compounds namely,
3-Amino-6-bromo-5-trifluoromethyl-pyrazine-2-carboxylic acid (5-cyclopropyl-2H-pyrazol-3-yl)-amide (Ex. 2),
3-Amino-6-bromo-5-trifluoromethyl-pyrazine-2-carboxylic acid (5-tert-butyl-2H-pyrazol-3-yl)-amide (Ex. 3),
3-Amino-6-bromo-5-trifluoromethyl-pyrazine-2-carboxylic acid (5-methyl-2H-pyrazol-3-yl)-amide (Ex. 4),
3-Amino-6-bromo-5-trifluoromethyl-pyridine-2-carboxylic acid (5-trifluoromethyl-2H-pyrazol-3-yl)-amide (Ex. 5)
3-Amino-6-bromo-5-trifluoromethyl-pyrazine-2-carboxylic acid (2H-pyrazol-3-yl)-amide (Ex. 6)
3-Amino-6-bromo-5-trifluoromethyl-pyridine-2-carboxylic acid (2H-pyrazol-3-yl)-amide (Ex. 7)

were prepared analogously to 3-amino-6-bromo-5-trifluoromethyl-pyrazine-2-carboxylic acid (5-trifluoromethyl-2H-pyrazol-3-yl)-amide (Example 1) from the appropriate starting compound (described herein) and amine. Some reactions were carried out using microwave radiation.

Example 8

3-Amino-6-pyrrolidin-1-yl-5-trifluoromethyl-pyrazine-2-carboxylic acid (5-trifluoromethyl-2H-pyrazol-3-yl)-amide To a stirred solution of 3-amino-6-bromo-5-trifluoromethyl-pyrazine-2-carboxylic acid (5-trifluoromethyl-2H-pyrazol-3-yl)-amide (Example 1) (40 mg, 0.095 mmol) in dry THF (2 ml) was added pyrrolidine (7.89 µL, 0.095 mmol). The resulting mixture was heated using microwave radiation at 120° C. for 35 minutes. The reaction mixture was partitioned between EtOAc (50 ml) and water (30 ml) and the organic portion was separated, (MgSO$_4$) and concentrated in vacuo to give the crude product as an orange oil. The crude product was purified using preparative TLC eluting with DCM: 1% MeOH to afford the title compound as an orange solid.

Example 9

3-Amino-6-morpholin-4-yl-5-trifluoromethyl-pyrazine-2-carboxylic acid (2H-pyrazol-3-yl)-amide A mixture comprising 3-amino-6-bromo-5-trifluoromethyl-pyrazine-2-carboxylic acid (2H-pyrazol-3-yl)-amide (Ex. 6) (42 mg, 0.120 mmol) and morpholine (1 ml, 11.3 mmol) was heated at 100-140° C. using microwave for 8 hours and 15 minutes. The reaction mixture was concentrated in vacuo and purification of the residue by preparative LC-MS afforded the title compound as a yellow solid.

Example 10

3-Amino-5-trifluoromethyl-pyrazine-2-carboxylic acid (2H-pyrazol-3-yl)-amide

The title compound was prepared analogously to 3-amino-6-bromo-5-trifluoromethyl-pyrazine-2-carboxylic acid (5-trifluoromethyl-2H-pyrazol-3-yl)-amide (Example 1) using 3-amino-5-trifluoromethyl-pyrazine-2-carboxylic acid (Intermediate 6) and 2H-pyrazol-3-ylamine.

Example 11

5-[(3-Amino-6-bromo-5-trifluoromethyl-pyrazine-2-carbonyl)-amino]-1H-[1,2,4]triazole-3-carboxylic acid The title compound was prepared analogously to 3-amino-6-bromo-5-trifluoromethyl-pyrazine-2-carboxylic acid (5-trifluoromethyl-2H-pyrazol-3-yl)-amide (Example 1) by replacing 3-(trifluoromethyl)-1H-pyrazol-5-amine with 5-amino-1H-[1,2,4]triazole-3-carboxylic acid methyl ester.

Example 12

3-Amino-6-dimethylamino-5-trifluoromethyl-pyrazine-2-carboxylic acid (2H-pyrazol-3-yl)-amide To a stirring solution of 3-amino-6-bromo-5-trifluoromethyl-pyrazine-2-carboxylic acid (2H-pyrazol-3-yl)-amide (Ex. 7)(50 mg, 0.142 mmol) in dry DMF (5 ml), diethanolamine (37.4 mg, 0.356 mmol) was added. The resulting solution was heated at 100° C. using microwave radiation for 66 hours. The reaction mixture was partitioned between EtOAc (20 ml) and water (20 ml), and the phases separated. The organic phase was washed with brine (10 ml), dried (MgSO$_4$) and concentrated in vacuo to give an orange solid. Purification of the crude product by chromatography on silica eluting with iso-hexane/EtOAc (gradient of 0 to 50% EtOAc) yielded the title compound as a yellow solid.

Example 13

3-Amino-6-bromo-5-trifluoromethyl-pyrazine-2-carboxylic acid (2H-[1,2,4]triazole-3-yl)amide The title compound was prepared analogously to 3-amino-6-bromo-5-trifluoromethyl-pyrazine-2-carboxylic acid (5-trifluoromethyl-2H-pyrazol-3-yl)-amide (Example 1) by replacing 3-(trifluoromethyl)-1H-pyrazol-5-amine with 1H-[1,2,4]triazole-5-amine.

Example 14

3-Amino-6-chloro-5-trifluoromethyl-pyrazine-2-carboxylic acid (2H-pyrazole-3-yl)amide The title compound was prepared analogously to 3-amino-6-bromo-5-trifluoromethyl-pyrazine-2-carboxylic acid (5-trifluoromethyl-2H-pyrazol-3-yl)-amide Example 1) using 3-amino-6-chloro-5-trifluoromethyl-pyrazine-2-carboxylic acid (Intermediate 7) and 2H-pyrazol-3-ylamine. The reaction was carried out using microwave radiation at 100° C. for 1 hour.

Example 15

3-Amino-6-bromo-5-trifluoromethyl-pyrazine-2-carboxylic acid (5-piperidin-1-ylmethyl-2H-pyrazol-3yl)-amide A mixture, comprising 3-amino-6-bromo-5-trifluoromethyl-pyrazine-2-carboxylic acid (Intermediate 2)(0.349 g, 1.221 mmol), 3-(piperidin-1-ylmethyl)-1H-pyrazol-5-amine (Intermediate 8) (0.220 g, 1.221 mmol), HATU (0.464 g, 1.221 mmol) and N-methylmorpholine (0.241 ml, 2.441 mmol) in DMF (5 ml) was stirred for 30 minutes at RT. The reaction mixture was diluted with water (20 ml) and the resulting yellow precipitate was filtered under vacuum and washed with water (20 ml). The resulting residue was loaded onto a SCX-2 cartridge eluting with MeOH followed by 7M NH$_3$ in MeOH. The methanolic ammonia fractions were concentrated in vacuo and the residue was triturated with EtOAc/iso-hexane to yield the title compound.

Example 16

3-Amino-6-bromo-N-(1H-pyrazolo[4,3-b]pyrazin-3-yl)-5-(trifluoromethyl)pyrazine-2-carboxamide A mixture comprising 3-amino-6-bromo-5-trifluoromethyl-pyrazine-2-carboxylic acid (Intermediate 2)(0.212 g, 0.740 mmol), 1H-pyrazolo[3,4-b]pyrazin-3-amine (0.10 g, 0.740 mmol), HATU (0.281 g, 0.740 mmol) and N-methylmorpholine (0.146 ml, 1.480 mmol) in DMF (5 ml) was stirred at RT for 45 minutes. The reaction mixture was diluted with water (25 ml) and the resulting orange precipitate was filtered under vacuum and washed with water (10 ml). The solid was purified by chromatography on silica, eluting with iso-hexane:EtOAc (gradient of 0 to 100% EtOAc) to afford the title compound as a yellow solid.

Example 17 tert-Butyl 3-(3-amino-6-bromo-5-(trifluoromethyl)pyrazine-2-carboxamido)-4,6-dihydropyrrolo[3,4-c]pyrazole-5(2H)-carboxylate A mixture comprising 3-Amino-6-bromo-5-trifluoromethyl-pyrazine-2-carboxylic acid (Intermediate 2)(0.102 g, 0.357 mmol), tert-butyl 3-amino-4,6-dihydropyrrolo[3,4-c]pyrazole-5(2H)-carboxylate (0.08 g, 0.357 mmol), HATU (0.136 g, 0.357 mmol) and N-methylmorpholine (0.071 ml, 0.713 mmol) in DMF (5 ml) was stirred at RT for 30 minutes. The reaction mixture was diluted with water (15 ml) and the resulting orange precipitate was filtered under vacuum and washed with water (10 ml). Purification of the resulting solid by chromatography on silica eluting with iso-hexane:EtOAc (gradient of 0 to 100% EtOAc) to afforded the title compound as a yellow solid.

Example 18

3-Amino-6-bromo-N-(1H-pyrazolo[4,3-b]pyrazin-3-yl)-5-(trifluoromethyl)picolinamide A mixture comprising 3-amino-6-bromo-5-trifluoromethyl-pyridine-2-carboxylic acid (Intermediate 3) (0.10 g, 0.351 mmol), 1H-pyrazolo[3,4-b]pyrazin-3-amine (0.047 g, 0.702 mmol), HATU (0.133 g, 0.351 mmol) and N-methylmorpholine (0.069 ml, 0.702 mmol) in DMF (5 ml) was stirred at 75° C. for 90 minutes. After cooling to RT, the mixture was diluted with water (30 ml) and the resulting orange precipitate was filtered under vacuum and washed with water. Purification of the resulting solid by chromatography on silica eluting with iso-hexane:EtOAc (gradient of 0 to 100% EtOAc) to afforded the title compound as an orange solid.

Example 19

3-Amino-6-bromo-N-(4-(pyridin-2-yl)-1H-pyrazol-5-yl)-5-(trifluoromethyl)pyrazine-2-carboxamide A mixture comprising 3-amino-6-bromo-5-trifluoromethyl-pyrazine-2-carboxylic acid (Intermediate 2) (0.179 g, 0.624 mmol), 5-amino-4-(pyridin-2-yl)-1H-pyrazole (0.1 g, 0.624 mmol), HATU (0.237 g, 0.624 mmol) and N-methylmorpholine (0.123 ml, 1.249 mmol) in DMF (5 ml) was stirred at 80° C. for 2.5 hours. After cooling to RT, the mixture was diluted with water (40 ml) and the resulting yellow precipitate was filtered under vacuum and washed with water (20 ml). MeOH (150 ml) was added to the solid and the suspension ultrasonicated to give a fine suspension. The suspension was filtered under vacuum and the solid was rinsed with MeOH (20 ml) and dried under vacuum at 45° C. for 1.5 hours to afford the title compound as a yellow solid.

Example 20

2-Amino-5-Iodo-N-(1H-pyrazol-5-yl)-4-(trifluoromethyl)benzamide hydrochloride

A mixture comprising 2-amino-5-iodo-4-trifluoromethyl benzoic acid (Intermediate 4) (0.414 g, 1.251 mmol), 1H-pyrazole-5-amine (0.104 g, 1.251 mmol) and HATU (0.476 g, 1.251 mmol) in DMF (5 ml) was treated with N-methylmorpholine (0.124 ml, 1.251 mmol) and the mixture was stirred at RT for 1 hour. The reaction mixture was diluted with 2M NaOH (20 ml) and after stirring for 5 minutes, the product was extracted with EtOAc (2×100 ml). The combined organic extracts were combined, dried (MgSO$_4$) and concentrated in vacuo. Purification of the resulting solid by chromatography on silica eluting with iso-hexane:EtOAc (gradient of 0 to 100 EtOAc) to afforded give a yellow oil. The oil was dried under vacuum at 45° C. overnight and the resulting white gum was stirred in a solution of 2M HCl in ether (2 ml) for 2 hours, filtered, washed with ether and dried on high vacuum at 45° C. to yield the title compound as a white solid.

Example 21

3-Amino-6-bromo-N-(1H-pyrazolo[3,4-b]pyridin-3-yl)-5-(trifluoromethyl)pyrazine-2-carboxamide A mixture comprising 3-amino-6-bromo-5-trifluoromethyl-pyrazine-2-carboxylic acid (Intermediate 2) (0.320 g, 1.118 mmol), 3-aminopyrazolo[3,4-b]pyridine (0.150 g, 1.118 mmol) and HATU (0.425 g, 1.118 mmol) in DMF (5 ml) was treated with N-methylmorpholine (0.111 ml, 1.118 mmol) and stirred at 80° C. overnight. After cooling to RT, the mixture was diluted with water (25 ml) and the resulting yellow precipitate was filtered under vacuum and washed with water. The crude material was purified by chromatography on silica eluting with iso-hexane:EtOAc (gradient of 0 to 100 EtOAc) to give the title compound as a yellow solid.

Example 22

3-Amino-6-chloro-N-(1H-pyrazol-5-yl)-5-(trifluoromethyl)picolinamide

A solution of 3-amino-6-chloro-5-trifluoromethyl-pyridine-2-carboxylic acid (Intermediate 5) (0.143 g, 0.594 mmol) in DMF (5 ml) was treated with HATU (226 mg, 0.594 mmol), 1H-pyrazole-5-amine (74.1 mg, 0.892 mmol) and 4-methylmorpholine (0.118 ml, 1.189 mmol). The mixture was stirred at RT for 30 minutes followed by 80° C. for 2 hours before cooling to RT. The reaction mixture was diluted with 2M NaOH (20 ml) and the product extracted with EtOAc (2×60 ml). The organics were combined, washed with brine (20 ml), dried over MgSO$_4$ and concentrated in vacuo to give a brown oil. This oil was taken up as a solution in DCM (2 ml), and after 5 minutes, a white precipitate was present. This was filtered under vacuum, washed with DCM and dried on high vacuum. The material was taken up in EtOAc (50 ml) and washed successively with 2M NaOH (2×20 ml), brine (10 ml), dried over MgSO$_4$ and concentrated in vacuo to give a yellow solid. This was taken up in MeOH (3 ml) and loaded onto a 10 g SCX-2 cartridge, eluted with MeOH (50 ml), then a solution of 7M NH$_3$ in MeOH (50 ml). The relevant fractions were combined and concentrated in vacuo to afford the title compound.

Example 23

Methyl 5-(3-amino-6-bromo-5-(trifluoromethyl)pyrazine-2-carboxamido)-1H-1,2,4-triazole-3-carboxylate To a solution of 3-amino-6-bromo-5-trifluoromethyl-pyrazine-2-carboxylic acid (Intermediate 2) (300 mg, 1.049 mmol) in dry DCM (10 ml) was added NEt$_3$ (0.322 ml, 2.308 mmol) followed by methyl 5-amino-1H-1,2,4-triazole-3-carboxylate (149 mg, 1.049 mmol). After stirring at RT for 5 minutes the reaction mixture was treated with PyBOP (546 mg, 1.049 mmol) and stirred for 3 hours. The mixture was partitioned between DCM (20 ml) and water (20 ml), shaken and separated. The organic portion was washed with water (20 ml), dried over MgSO$_4$, filtered and concentrated in vacuo to give an orange oil. Purification of the crude residue by chromatography on silica eluting with 0-100% EtOAc in iso-hexane, followed by 0-35% MeOH in EtOAc afforded a yellow oil. Trituration of the oil with EtOAc/iso-hexane followed by MeCN/water afforded the title compound as a yellow solid.

Example 24

3-Amino-N-(3-benzyl-1H-1,2,4-triazol-5-yl)-6-bromo-5-(trifluoromethyl)pyrazin-2-carboxamide The title compound was prepared analogously to Example 23 from 3-amino-6-bromo-5-trifluoromethyl-pyrazine-2-carboxylic acid (Intermediate 2) and 3-benzyl-1H-1,2,4-triazol-5-amine.

Example 25.1

3-Amino-6-(4-fluorophenyl)-N-(1H-pyrazol-3-yl)-5-(trifluoromethyl)picolinamide

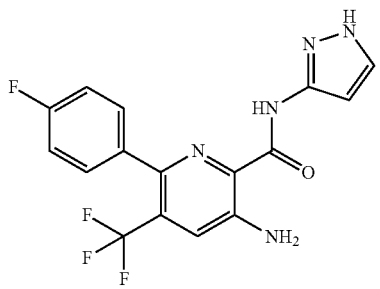 [SMILES: Nc1cc(C(F)(F)F)c(-c2ccc(F)cc2)nc1C(=O)Nc1cc[nH]n1]

Step 1: Methyl 3-amino-6-(4-fluorophenyl)-5-(trifluoromethyl)picolinate

3-Amino-6-bromo-5-trifluoromethyl-pyridine-2-carboxylic acid methyl ester (Intermediate 3D) (200 mg, 0.669 mmol), 4-fluorophenylboronic acid (94 mg, 0.669 mmol) and 1,1'bis(diphenylphosphoshio)ferrocene palladium dichloride (Apollo) were suspended in THF (2 ml) and 1M $Cs_2CO_3$ (0.667 ml). The vial was flushed with $N_2$, sealed and heated at 160° C. for 15 minutes using microwave radiation. The reaction mixture was partitioned between EtOAc (50 ml) and water (50 ml). The organic portion was separated and washed with brine (30 ml), dried over $MgSO_4$, filtered and concentrated in vacuo. Purification by chromatography on silica eluting with 0-80% EtOAc in iso-hexane afforded the title compound;

LCMS: Rt=1.47 mins, [M+H]+ 315.1; Method 2min-LC_v002.

Step 2: 3-Amino-6-(4-fluorophenyl)-5-(trifluoromethyl)picolinic acid

To a stirred solution of methyl 3-amino-6-(4-fluorophenyl)-5-(trifluoromethyl)picolinate (step 1) (6.00 mmol) in EtOH (5 ml) was added 2M NaOH (3 ml, 6.00 mmol) and the solution was stirred at RT for 15 minutes. The resulting mixture was diluted with water (10 ml) and the pH was adjusted to pH 6 using 1M HCl. The mixture was extracted with DCM (2×10 ml) and the phases were separated using a phase separating cartridge. The combined organic extracts were concentrated in vacuo and used in the next step without further purification;

LCMS: Rt=1.42 mins, [M+H]+ 301.1; Method 2min-LC_v002.

Step 3: 3-Amino-6-(4-fluorophenyl)-N-(1H-pyrazol-3-yl)-5-(trifluoromethyl)picolinamide A stirred solution of 3-amino-6-(4-fluorophenyl)-5-(trifluoromethyl)picolinic acid (0.167 mmol) in dry NMP (2 ml) was treated with 1H-pyrazol-3-amine (0.183 mmol). After stirring at RT, triethylamine (0.366 mmol) was added and stirring continued for 5 minutes. HATU (0.183 mmol) was added and the resulting mixture was sealed and heated at 100° C. for 1 hour using microwave radiation. The mixture was partitioned between EtOAc (25 ml) and 1M NaOH (25 ml). The organic portion was separated, washed with water (25 ml), dried over $MgSO_4$ and concentrated in vacuo. Purification by mass directed LCMS eluting with TFA/MeCN/water afforded the title compound as a TFA salt. The salt was partitioned between EtOAc (10 ml) and sodium bicarbonate (10 ml). The organic portion was separated, passed through phase separating cartridge and concentrated in vacuo to afford the title compound;

LCMS: Rt=1.58 mins, [M+H]+ 366.2; Method 2min-LC_v002.

1H NMR (400 MHz, DMSO-d6) δ 12.6 (1H, s), 10.2 (1H, s), 7.82 (1H, s), 7.78 (1H, s), 7.62 (2H, m), 7.3-7.4 (4H, m), 6.72 (1H, s).

The compounds of the following tabulated Examples (Table 2) were prepared by a similar method to that of Example 25 from the appropriate starting compound and amine.

TABLE 2

| Ex. | Structure | Name | Retention Time, [M+ H]+, 1H NMR |
|---|---|---|---|
| 25.2 | 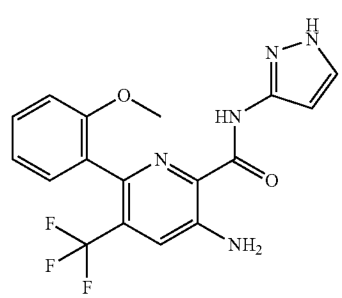 | 3-Amino-6-(4-chloro-2-methyl-phenyl)-5-trifluoro methyl-pyridine-2-carboxylic acid (2H-pyrazol-3-yl)-amide | Rt 1.66 mins; [M + H]+ 396.2 Method 2minLC_v003 1H NMR (400 MHz, DMSO-d6) δ 12.6 (1H, s), 10.1 (1H, s), 7.84 (1H, s), 7.76 (1H, s), 7.5 (1H, s), 7.34-7.44 (3H, m), 7.3 (1H, d), 6.7 (1H, s), 2.1 (3H, s) |

TABLE 2-continued

| Ex. | Structure | Name | Retention Time, [M+ H]+, 1H NMR |
|---|---|---|---|
| 25.3 | 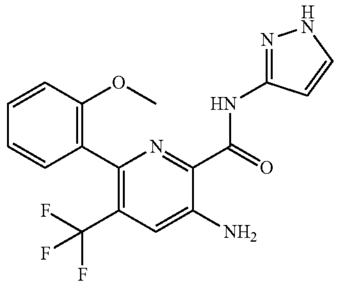 [SMILES: COc1ccccc1-c1nc(C(=O)Nc2cc[nH]n2)c(N)cc1C(F)(F)F] | 5-Amino-2'-methoxy-3-trifluoromethyl-[2,3']bipyridinyl-6-carboxylic acid (1H-pyrazol-3-yl)-amide | Rt 1.43 mins; [M + H]+ 379.2 Method 2minLC_v003 1H NMR (400 MHz, DMSO-d6) δ 12.6 (1H, s), 10.16 (1H, s), 8.34 (1H, m), 7.8 (2H, m), 7.74 (1H, s), 7.38 (2H, br s), 7.18 (1H, m), 6.7 (1H, s), 3.89 (3H, s) |

Examples 26.1-26.3

The compounds of the following tabulated Examples (Table 3) were prepared according to the following general procedure:

To a microwave vial containing a commercially available boronic acid (0.100 ml) was added a solution of 3-amino-6-bromo-5-trifluoromethyl-pyridine-2-carboxylic acid (2H-pyrazol-3-yl)-amide (Ex. 7) (0.100 mmol) in 1,4-dioxane (1 ml), a solution of K$_2$CO$_3$ (0.300 mmol) in water (167 μl) followed by Pd(PPh$_3$)$_2$Cl$_2$ (0.7 mg, 1.000 μmol). The mixture was heated at 160° C. using microwave radiation for 30 minutes. The resulting mixture was passed through a pre-wetted (MeOH) SCX-2 (1 g) cartridge eluting with MeOH followed by 3M NH$_3$ in MeOH. The methanolic ammonia fractions were concentrated in vacuo and dried under vacuum. The crude product was purified by preparative LCMS to afford the desired product.

TABLE 3

| Ex. | Structure | Name | Retention Time, [M+ H]+, 1H NMR |
|---|---|---|---|
| 26.1 | 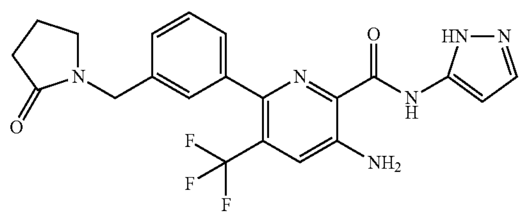 [SMILES: Nc1cc(C(F)(F)F)c(-c2cccc(CN3CCCC3=O)c2)nc1C(=O)Nc1ccn[nH]1] | 3-Amino-6-[3-(2-oxo-pyrrolidin-1-ylmethyl)-phenyl]-5-trifluoromethyl-pyridine-2-carboxylic acid (2H-pyrazol-3-yl)-amine | Rt 1.40 mins; [M + H]+ 445.2 Method LowpH_v003 |
| 26.2 | 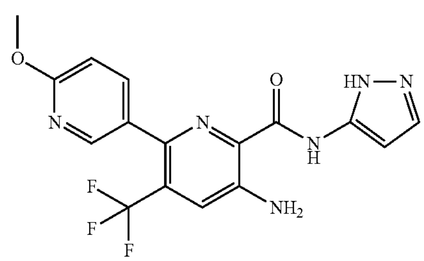 [SMILES: COc1ccc(-c2nc(C(=O)Nc3ccn[nH]3)c(N)cc2C(F)(F)F)cn1] | 5-Amino-6'-methoxy-3-trifluoromethyl-[2,3']bipyridinyl-6-carboxylic acid (2H-pyrazol-3-yl)-amide | Rt 1.42 mins; [M + H]+ 379.2 Method LowpH_v003 |
| 26.3 | 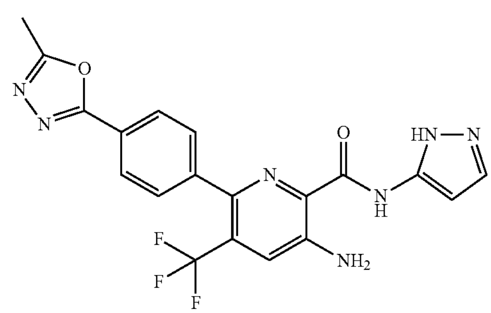 [SMILES: Cc1nnc(-c2ccc(-c3nc(C(=O)Nc4ccn[nH]4)c(N)cc3C(F)(F)F)cc2)o1] | 3-Amino-6-[4-(5-methyl-[1,3,4]oxadiazol-2-yl)-phenyl]-5-trifluoromethyl-pyridine-2-carboxylic acid (2H-pyrazol-3-yl)-amide | Rt 1.40 mins; [M + H]+ 430.2 Method LowpH_v003 |

Examples 27

3-Amino-5,6-bis-trifluoromethyl-pyrazine-2-carboxylic acid (4-methyl-2H-pyrazol-3-yl)-amide

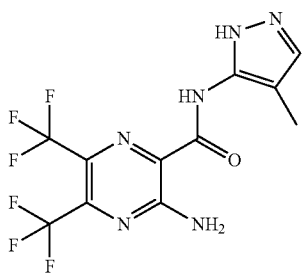 [SMILES: Cc1cn[nH]c1NC(=O)c1nc(C(F)(F)F)c(C(F)(F)F)nc1N]

The title compound is prepared from Intermediate 1AA and 4-methyl-1H-pyrazol-5-amineanalogously to Example 1.0

LCMS: Rt=1.43 mins; [M+H]+ 354.9; Method 2min-LC_v003

1H NMR (400 MHz, DMSO-d6) δ 12.5 (1H, s), 10.2 (1H, s), 8.6-8.8 (1H, broad hump), 8.4-8.6 (1H, broad hump), 7.54 (1H, s), 1.92 (3H, s)

Preparation of Intermediates

Intermediate 1

3-Amino-5-trifluoromethyl-pyrazine-2-carboxylic acid ethyl ester

Intermediate 1A

Carbamimidoyl-nitroso-acetic acid ethyl ester

To a solution of 2M ammonia in Ethanol (152 ml, 0.304 mmol) at 0° C. to 5° C., ethyl ethoxycarbonylacetimidate HCl (25 g, 0.127 mmol) was added over 30 minutes. The reaction was stirred vigorously at this temperature for 3 hours, after which a solution of sodium nitrile in water (9.63 g, 0.139 mmol) was added in a single portion. The pH of the mixture was adjusted to pH6 with the addition of 5N HCl. The reaction mixture was left to stir at RT overnight. The yellow precipitate formed was filtered under vacuum, washed with water and dried to give the title compound;

$^1$H NMR (400 MHz, DMSO-d6) δ 10.1 (2H, br s), 7.6 (2H, br s), 4.3 (2H, q), 1.3 (3H, t).

Intermediate 1B

Amino-carbamimidoyl-acetic acid ethyl ester

To a solution of carbamimidoyl-nitroso-acetic acid ethyl ester (5.5 g, 31.4 mmol) in ethanol/5M HCl (1:1 ratio, 250 ml) was added 10% Pd/C (1.3 g). The reaction mixture was hydrogenated ($H_{2(g)}$) at low pressure over 2 nights. The Pd/C was filtered through Celite® (filter material) and the filtrate reduced in vacuo to give the title compound as a white solid. This was taken through to the next step as crude.

Intermediate 1

3-Amino-5-trifluoromethyl-pyrazine-2-carboxylic acid ethyl ester

To a mixture of amino-carbamimidoyl-acetic acid ethyl ester (2 g, 9.22 mmol) and water (50 ml), a 20% aqueous solution of trifluoropyruvic aldehyde (2.32 g, 18.43 mmol) was added. To this mixture, sodium acetate (5.29 g, 64.52 mmol) was added (pH of the reaction mixture was pH5). The reaction mixture was left to stir at RT overnight. The resultant precipitate was filtered under vacuum purification by chromatography on silica eluting with iso-hexane:EtOAc (gradient of 0 to 10% EtOAc) afforded the title compound $^1$H NMR (400 MHz, DMSO-d6) δ 8.4 (1H, s), 7.8 (2H, br s), 4.4 (2H, q), 1.4 (3H, t).

Intermediate 1AA

3-Amino-5,6-bis(trifluoromethyl)pyrazine-2-carboxylic acid

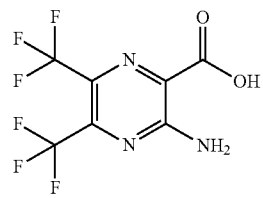 [SMILES: Nc1nc(C(F)(F)F)c(C(F)(F)F)nc1C(=O)O]

Step 1: Ethyl 3-amino-5,6-bis(trifluoromethyl)pyrazine-2-carboxylate

The title compound was prepared analogously to Intermediate 1 by replacing trifluoropyruvic aldehyde with 1,1,1,4,4,4-hexafluorobutane-2,3-dione;

LCMS Rt=4.72 minutes, [M+H]+ 304.2/326.1 Method 10minLC_v002.

Step 2: 3-Amino-5,6-bis(trifluoromethyl)pyrazine-2-carboxylic acid

To a stirring solution of ethyl 3-amino-5,6-bis(trifluoromethyl)pyrazine-2-carboxylate (300 mg, 0.990 mmol) in EtOH (10 ml), 2M NaOH (0.495 ml, 0.990 mmol) was added dropwise over 1 minute. After stirring at RT for 30 minutes the reaction mixture was poured into water (30 ml) and the pH was adjusted to pH 4 by addition of 1M HCl.

The mixture was extracted with EtOAc (2×50 ml) and the combined organic extracts were washed with brine (30 ml), dried over MgSO$_4$ (5 g), filtered and concentrated in vacuo to afford the title compound as an off white crystalline solid;

$^1$H NMR (400 MHz, DMSO-d6) δ 8.6-9.2 (2H, broad hump), 7.8-8.3 (2H, broad hump), 4.4 (2H, q), 1.32 (3H, t).

Intermediate 2

3-Amino-6-bromo-5-trifluoromethyl-pyrazine-2-carboxylic acid

Intermediate 2A

3-Amino-6-bromo-5-trifluoromethyl-pyrazine-2-carboxylic acid ethyl ester

To a solution of 3-amino-5-trifluoromethyl-pyrazine-2-carboxylic acid ethyl ester (Intermediate 1) (30 mg, 0.13 mmol) in acetic acid (5 ml), sodium carbonate (15 mg, 0.14 mmol) was added. To this mixture, half the contents of a solution of bromine (7 μL, 0.13 mmol) in acetic acid (5 ml) was added, followed by the addition of sodium carbonate ((15 mg, 0.14 mmol). The remaining solution of bromine in acetic acid was added and the reaction mixture was left to stir at RT for 2 hours. The mixture was diluted with water and the resulting yellow precipitate was filtered under vacuum to afford the title compound.

Intermediate 2

3-Amino-6-bromo-5-trifluoromethyl-pyrazine-2-carboxylic acid

To a stirring solution of 3-amino-5-trifluoromethyl-pyrazine-2-carboxylic acid ethyl ester
(10 g, 31.8 mmol) in ethanol (20 ml), 2M NaOH (20 ml, 31.8 mmol) was added.
The resulting solution was stirred at RT for 5 minutes and poured into water (50 ml). The pH was adjusted to pH6 with the addition of 1M HCl. The resulting suspension was filtered under vacuum, washed with water (20 ml) and dried to afford the title compound;
MS m/z 287 [M+H]$^+$. $^1$H NMR (400 MHz, DMSO-d6) δ 7.98 (2H, s).

Intermediate 3

3-Amino-6-bromo-5-trifluoromethyl-pyridine-2-carboxylic acid

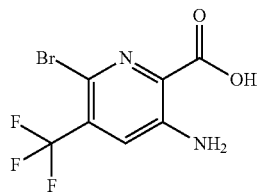 [SMILES: Nc1cc(C(F)(F)F)c(Br)nc1C(=O)O]

Intermediate 3A

2-Bromo-3-nitro-5-trifluoromethyl-pyridine

3-Nitro-5-(trifluoromethyl)pyridin-2-ol (31.00 g, 149 mmol) was dissolved in acetonitrile (250 ml) to give a dark brown solution. Phosphorus(V) oxybromide (85 g, 298 mmol) was added and the mixture was heated at reflux for 4 hours and then stirred at RT overnight. The reaction mixture was quenched by pouring into vigorously stirring water (600 ml) containing sodium hydrogencarbonate (110 g). The dark brown mixture was extracted with DCM (3×200 ml) and the organic phase was washed with water (200 ml) and brine (100 ml), dried (MgSO$_4$) and concentrated in vacuo to afford the title product as a brown oil. $^1$H-NMR: [400 MHz, CDCl$_3$, δ$_H$ 8.87 (1H, d, J=1.4 Hz, ArH), 8.39 (1H, d, J=1.9 Hz, ArH).

Intermediate 3B

3-Nitro-5-trifluoromethyl-pyridine-2-carbonitrile

2-Bromo-3-nitro-5-trifluoromethyl-pyridine (10.00 g, 36.87 mmol) was dissolved in toluene (250 ml) with stirring to give a pale yellow solution. Tetrabutylammonium bromide (11.90 g, 36.9 mmol) was added followed by copper(I) cyanide (9.92 g, 111 mmol) and the mixture was heated at reflux for 9 hrs. After cooling to RT, the reaction mixture was partitioned between water (750 ml) and EtOAc (750 ml). The organic fractions were combined, washed with water (2×250 ml) and brine (100 ml), dried dried (MgSO$_4$) and concentrated in vacuo to afford the title product. $^1$H-NMR: [400 MHz, DMSO-d$_6$ δ$_H$ 9.55 (1H, m, ArH), 9.24 (1H, m, ArH)

Intermediate 3C

3-Amino-5-trifluoromethyl-pyridine-2-carboxylic acid methyl ester

3-Nitro-5-trifluoromethyl-pyridine-2-carbonitrile (6.5 g, 29.9 mmol) was dissolved in EtOAc (150 ml) to give a pale yellow solution. 10% Palladium on activated carbon (3.19 g, 2.99 mmol) was added and the reaction mixture stirred under an atmosphere of hydrogen for 18 hours. The reaction mixture was filtered and concentrated in vacuo. The crude residue was dissolved in HCl conc. (45 ml) and heated to reflux for 24 hours. The reaction mixture was allowed to cool to RT and concentrated in vacuo. The solid was dissolved in MeOH (200 ml) and sulfuric acid (8 ml) was added. The resulting solution was heated at reflux for 84 hours. The reaction was allowed to cool to RT, then neutralised by addition of 10% NaHCO$_{3(aq)}$ (600 ml). The product was extracted into DCM (3×200 ml) and the combined organic phases were washed with water (200 ml), brine (50 ml), (MgSO$_4$) and concentrated in vacuo. The resulting solid was purified by chromatography on silica: Eluent gradient: isohexane (500 ml), 10% EtOAc in isohexane (1000 ml), 20% EtOAc in isohexane (1500 ml) to afford the titled compound as a pale yellow solid $^1$H-NMR: [400 MHz, DMSO-d$_6$, δ$_H$ 8.13 (1H, d, J=1.7 Hz, ArH), 7.60 (1H, d, J=1.3 Hz, ArH), 7.01 (2H, br, NH$_2$), 3.85 (3H, s, ArOCH$_3$), m/z 221.1 [M+H]$^+$ Intermediate 3D 3-Amino-6-bromo-5-trifluoromethyl-pyridine-2-carboxylic acid methyl ester 3-Amino-5-trifluoromethyl-pyridine-2-carboxylic acid methyl ester (9.49 g, 43.16 mmol) was dissolved in water (300 ml). Sulfuric acid (4.60 ml, 86 mmol) was added followed by dropwise addition over 30 minutes of a solution of bromine (2.222 ml, 43.1 mmol) in acetic acid (29.6 ml, 517 mmol). The reaction mixture was stirred at RT for 18 hours. A further 100 ml of water was added, followed by a further 0.25 equivalents of the bromine/AcOH mixture (550 μL bromine in 7.4 ml AcOH) and the reaction mixture stirred at RT for an additional 90 minutes. The reaction mixture was diluted with 500 ml water and neutralised by addition of solid NaHCO$_3$ (~85 g). The suspension was extracted with DCM (3×300 ml) and the combined organic phases washed with sat.NaHCO$_{3(aq)}$ (250 ml), water (250 ml) and brine (100 ml), dried (MgSO$_4$) and concentrated in vacuo. The crude material was recrystallised from boiling MeOH (~300 ml) to give the title product as a pale orange solid m/z 301.0 (95) [M+H]$^+$ $^1$H-NMR: (400 MHz, DMSO-d$_6$ δ$_H$ 7.77 (1H, s, ArH), 7.17 (2H, s, NH$_2$), 3.86 (3H, s, ArCO$_2$CH$_3$).

Intermediate 3

3-Amino-6-bromo-5-trifluoromethyl-pyridine-2-carboxylic acid

3-Amino-6-bromo-5-trifluoromethyl-pyridine-2-carboxylic acid methyl ester (1.40 g, 4.68 mmol) was suspended in MeOH (15 ml); Sodium hydroxide (2.0 M aqueous solution) (14.04 ml, 28.1 mmol) was added and the suspension was stirred at RT overnight. The reaction mixture was concentrated in vacuo and the resulting residue was dissolved in water (100 ml) and then acidifed by the addition of 5.0M HCl(aq). The product was extracted into ethyl acetate (2×75 ml) and the combined organic extracts were washed with water (50 ml), brine (25 ml), dried (MgSO$_4$) and concentrated in vacuo to afford the title product as a yellow solid. $^1$H-NMR: [400 MHz, DMSO-d$_6$, $\delta_H$ 13.24 (1H, br s, CO$_2$H), 7.74 (1H, s, ArH), 7.17 92H, br s ArNH$_2$). m/z 285.1, 287.1 [M+H]$^+$

Intermediate 4

2-Amino-5-iodo-4-trifluoromethyl benzoic acid

Intermediate 4A

2-Amino-4-trifluoromethyl-benzoic acid methyl ester

A solution of 2-amino-4-(trifluoromethyl)benzolic acid (75 g, 366 mmol) in MeOH (750 ml) was treated dropwise with sulfuric acid (48.7 ml) over ~15 minutes (exotherm temperature 34° C.) maintaining the temperature at 20° C. The resulting mixture was heated to 65° C. for 24 hours. After cooling to RT, the mixture was diluted with water (750 ml) under stirring. The resulting precipitate was filtered and the solid was slurried in water (500 ml). Saturated sodium bicarbonate (1 L) was added to take the pH to pH9 and the mixture was extracted with diethyl ether (3×330 ml). The combined organic extracts were washed with brine (700 ml), dried (MgSO$_4$) and concentrated in vacuo to afford the title product. MS m/z 220 [M+H]$^+$.

Intermediate 4B

2-Amino-5-Iodo-4-trifluoromethyl-benzoic acid methyl ester

2-Amino-4-trifluoromethyl-benzoic acid methyl ester, (48 g, 219 mmol) was dissolved in MeOH (750 ml). Silver sulfate (68.3 g, 219 mmol) and iodine (55.6 g, 219 mmol) was added and rinsed in with MeOH (50 ml). The reaction mixture was left for 1 hour at RT. The reaction mixture was filtered under vacuum and the filtrate concentrated in vacuo. The residue was taken up in MeOH (100 ml) and water (10 ml) and the mixture heated at 80° C. The crude solution was hot filtered to remove residual inorganics and the warm filtrate was poured slowly into water (750 ml) with vigorous stirring. The mixture was left to particulate for 10 minutes and filtered to give the title compound as an orange solid. MS m/z 345 [M+H]$^+$.

Intermediate 4

2-Amino-5-iodo-4-trifluoromethyl benzoic acid

2-Amino-5-Iodo-4-trifluoromethyl-benzoic acid methyl ester (5.0 g, 14.49 mmol) was dissolved in MeOH (100 ml) to give an orange solution. 2M NaOH (aq) (50.7 ml, 101 mmol) was added and the orange solution was stirred at RT overnight. The reaction was stripped of MeOH under reduced pressure and the remaining aqueous solution was acidified by addition of conc.HCl$_{(aq)}$ to the stirred solution until a thick precipitate formed. The solid was filtered, washed with water (2×10 ml) before drying under vacuum @ 40° C. for 48 hours to give the title compound as a yellow/brown solid. $^1$H NMR (400 MHz, DMSO-d6) δ 7.98 (2H, s).

Intermediate 5

3-Amino-6-chloro-5-trifluoromethyl-pyridine-2-carboxylic acid

3-Amino-6-bromo-5-trifluoromethyl-pyridine-2-carboxylic acid methyl ester (Intermediate 3D) (100 mg, 0.334 mmol) was dissolved in 5M HCl (2.5 ml) and heated at 150° C., 5.5 bar in the microwave for 1 hour. The reaction mixture was purified by reverse phase chromatography eluting with water/MeCN to afford the title compound. MS m/z 241 [M+H]$^+$. $^1$H NMR (400 MHz, DMSO-d6) δ 13.33 (1H, br hump), 7.79 (1H, s), 7.19 (2H, br s

Intermediate 6

3-Amino-5-trifluoromethyl-pyrazine-2-carboxylic acid

To a stirring solution of 3-amino-5-trifluoromethyl-pyrazine-2-carboxylic acid ethyl ester (Intermediate 1) (0.5 g, 2.126 mmol) in dry ethanol (5 ml), 2M NaOH (5.32 ml, 10.63 mmol) was added. The yellow solution was stirred at RT. After 5 minutes, the reaction mixture was poured into water (15 ml) and the pH adjusted to pH 6 by addition of 1M HCl. The yellow precipitate formed was filtered under vacuum and dried to yield the title compound. $^1$H NMR (400 MHz, DMSO-d6) δ 13.65 (1H, s), 8.3 (1H, s), 7.86 (2H, br s)

Intermediate 7

3-Amino-6-chloro-5-trifluoromethyl-pyrazine-2-carboxylic acid

Intermediate 7A

3-Amino-6-chloro-5-trifluoromethyl-pyrazine-2-carboxylic acid ethyl ester

3-Amino-6-bromo-5-trifluoromethyl-pyrazine-2-carboxylic acid (Intermediate 2)(200 mg, 0.637 mmol, 1 eq) in 4M HCl in dioxane (2 ml) was heated at 110° C. using microwave radiation for 30 minutes, then at 100° C. for 1.5 hours. The reaction mixture was poured into water (30 ml) and neutralised with saturated NaHCO$_3$. The product was extracted with EtOAc (2×20 ml), the organics combined and washed with brine (20 ml), dried (MgSO$_4$) and concentrated in vacuo to give a yellow oil. The crude material was taken up in MeOH (3 ml) and triturated with water (15 ml) to give the title compound as a pale yellow solid. MS m/z 270 [M+H]$^+$ 1H NMR (400 MHz, DMSO-d6) δ 7.96 (2H, broad hump), 4.4 (2H, q), 1.34 (3H, t)

Intermediate 7

3-Amino-6-chloro-5-trifluoromethyl-pyrazine-2-carboxylic acid

To a stirring solution of 3-amino-6-chloro-5-trifluoromethyl-pyrazine-2-carboxylic acid ethyl ester (Intermediate 7A) (165 mg, 0.612 mmol) in dry ethanol (10 ml), 2M NaOH (0.306 ml, 0.612 mmol) was added. After stirring at RT for 10 minutes, the reaction mixture was poured into water (30 ml) and the pH taken to 6 with the addition of 1M HCl. The product was extracted with EtOAc (2×30 ml). The organics were combined and washed with brine (20 ml), dried (MgSO$_4$) and concentrated in vacuo. The crude material was purified by preparative LC-MS using 0.1% TFA/MeCN/Water system to afford the title compound. MS m/z 244 [M+H]+

Intermediate 8

3-(Piperidin-1-ylmethyl)-1H-pyrazol-5-amine

NaH (0.234 g, 5.84 mmol) in dry toluene (5 ml) was heated to 80° C. A mixture of acetonitrile (0.229 ml, 4.38 mmol), ethyl 1-piperidineacetate (0.5 g, 2.92 mmol) and toluene (3 ml) was added dropwise to the hot reaction mixture. The mixture was stirred at 80° C. for 1.5 hours and after cooling to RT, quenched by the addition of water (6 ml). Hydrazine hydrate (0.142 ml, 2.92 mmol) was added and reaction mixture reheated to 80° C. for 3 hours. The reaction mixture was acidified with 2N HCl (aq.) to pH 2 and loaded onto a SCX-2 cartridge eluting with MeOH followed by 7M $NH_3$ in MeOH. The methanolic ammonia fractions were concentrated in vacuo to afford an oil. 4N HCl in dioxane (15 ml) was added to the yellow oil and the resulting suspension was filtered and washed with iso-hexane to yield the title compound.

MS m/z 181.1 [M+H]+. $^1$H NMR (400 MHz, DMSO-d6) δ 10.95 (1H, br), 6.28 (1H, br), 4.24 (2H, s), 3.30 (2H, br d), 2.83 (2H, br), 1.78 (4H, m), 1.68 (2H, br d), 1.37 (2H, br).

The following are further embodiments of the invention:

Embodiment 1

A compound of Formula I

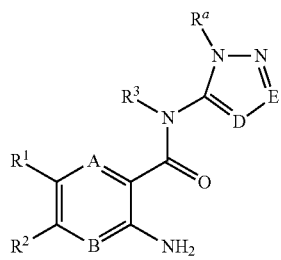

or a pharmaceutically acceptable salt or solvate thereof, wherein:

A is N or $CR^4$;

B is N or $CR^5$;

D is N or $CR^6$;

E is N or $CR^7$, provided that D and E are not both N;

$R^1$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; halogen; $SO_2NR^8R^9$; $SO_2R^{10}$; S—$C_1$-$C_8$ alkyl optionally substituted by one or more halogen atoms; S—$C_6$-$C_{14}$ aryl; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; CN; $NR^{11}R^{12}$; $CONR^{13}R^{14}$; $NR^{13}SO2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;

$R^2$ is selected from $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; Cl; Br; I; $SO_2NR^8R^9$; $SO_2R^{10}$; S—$C_1$-$C_8$ alkyl optionally substituted by one or more halogen atoms; S—$C_6$-$C_{14}$ aryl optionally substituted by one or more Z substituents; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; CN; $CONR^{13}R^{14}$; $NR^{13}SO2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;

$R^a$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $SO_2R^{10}$; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; $C(O)R^{15}$ and $CO_2R^{15}$, wherein the cycloalkyl, cycloalkenyl, aryl and heterocyclyl groups are each optionally substituted by one or more Z substituents;

$R^3$ and $R^4$ are each independently selected from H and $C_1$-$C_8$ alkyl optionally substituted by one or more halogen atoms;

$R^5$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; halogen; —($C_0$-$C_4$ alkyl)-$C_6$-$C_{14}$ aryl; and —($C_0$-$C_4$ alkyl)-3 to 14 membered heterocyclic group, wherein the heterocyclic group contains at least one heteroatom selected from N, O and S; wherein the cycloalkyl, cycloalkenyl, aryl and heterocyclyl groups are each optionally substituted by one or more Z substituents;

$R^6$ and $R^7$ are each independently selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; and —($C_0$-$C_4$ alkyl)-$CO_2R^{15}$, wherein the cycloalkyl, cycloalkenyl, aryl and heterocyclyl groups are each optionally substituted by one or more Z substituents; or $R^6$ and $R^7$ are each independently a group of the formula:

—$(CH_2)_n$—X—$(CH_2)_m$—$NR^{17}R^{18}$; or $R^6$ and $R^7$ together with the carbon atoms to which they are bound form a 5 to 8 membered carbocyclic ring system or a 5 to 8 membered heterocyclic ring system containing one or more heteroatoms selected from N, O and S, wherein the ring system is optionally substituted by one or more Z substituents;

X is absent, O, S, CO, SO, $SO_2$ or $CH_2$;

n and m are each independently selected from 0, 1, 2 and 3;

$R^8$, $R^{11}$, $R^{13}$ and $R^{17}$ are each independently selected from H, $C_1$-$C_8$ alkyl optionally substituted by one or more halogen atoms, $C_3$-$C_{10}$ cycloalkyl and —($C_1$-$C_4$ alkyl)-$C_3$-$C_8$ cycloalkyl;

$R^9$, $R^{10}$, $R^{12}$, $R^{14}$, $R^{15}$, $R^{16}$ and $R^{18}$ are each independently selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; and —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;

Z is independently selected from OH; aryl; O-aryl; benzyl; O-benzyl; $C_1$-$C_6$ alkyl optionally substituted by one or more OH groups or $NH_2$ groups; $C_1$-$C_6$ alkyl optionally substituted by one or more halogen atoms; $C_1$-$C_6$ alkoxy optionally substituted by one or more OH groups or $C_1$-$C_4$ alkoxy; $NR^{18'}(SO_2)R^{21}$; $(SO_2)NR^{19}R^{21}$; $(SO_2)R^{21}$; $NR^{18'}C(O)R^{21}$; $C(O)NR^{19}R^{21}$; $NR^{19}C(O)NR^{19}R^{21}$; $NR^{18'}C(O)OR^{19}$; $NR^{19}R^{21}$; $C(O)OR^{19}$; $C(O)R^{19}$; $SR^{19}$; $OR^{19}$; oxo; CN; $NO_2$; halogen; and —$(C_0$-$C_4$ alkyl)-3 to 14 membered heterocyclic group, wherein the heterocyclic group contains at least one heteroatom selected from N, O and S, optionally substituted by one or more groups selected from halogen, oxo, $C_1$-$C_6$ alkyl and $C(O)C_1$-$C_6$ alkyl; $R^{18'}$ and $R^{20}$ are each independently selected from H and $C_1$-$C_6$ alkyl;

$R^{19}$ and $R^{21}$ are each independently selected from H; $C_1$-$C_8$ alkyl; $C_3$-$C_8$ cycloalkyl; $C_1$-$C_4$ alkoxy-$C_1$-$C_4$ alkyl; $(C_0$-$C_4$ alkyl)-aryl optionally substituted by one or more groups selected from $C_1$-$C_6$ alkyl, $C_1$-$C_6$ alkoxy and halogen; $(C_0$-$C_4$ alkyl)- 3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; $(C_0$-$C_4$ alkyl)-O-aryl optionally substituted by one or more groups selected from $C_1$-$C_6$ alkyl, $C_1$-$C_6$ alkoxy and halogen; and $(C_0$-$C_4$ alkyl)- O-3- to 14-membered heterocyclic group, the heterocyclic group including one or more heteroatoms selected from N, O and S, optionally substituted by one or more groups selected from halogen, $C_1$-$C_6$ alkyl and $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy;

for use in the treatment of a disease or disorder mediated by CFTR.

Embodiment 2

A compound according to Embodiment 1, wherein A is N.

Embodiment 3

A compound according to Embodiment 1 or Embodiment 2, wherein $R^1$ is selected from H; $C_1$-$C_8$ alkyl optionally substituted by one or more halogen atoms; halogen; $C_6$-$C_{14}$ aryl; —$(C_0$-$C_4$ alkyl)-3 to 14 membered heterocyclic group, wherein the heterocyclic group contains at least one heteroatom selected from N, O and S; and $NR^{11}R^{12}$, wherein the aryl and heterocyclic groups are each optionally substituted by one or more Z substituents.

Embodiment 4

A compound according to any preceding embodiment, wherein $R^2$ is $C_1$-$C_8$ alkyl optionally substituted by one or more halogen atoms; $C_3$-$C_{10}$ cycloalkyl; or —$C_1$-$C_4$ alkyl-$C_3$-$C_8$ cycloalkyl.

Embodiment 5

A compound according to Embodiment 4, wherein $R^2$ is $CF_3$.

Embodiment 6

A compound according to any preceding embodiment, wherein $R^3$ is H or methyl.

Embodiment 7

A compound according to any preceding embodiment, wherein $R^a$ is H.

Embodiment 8

A compound according to any preceding embodiment, wherein E is $CR^7$.

Embodiment 9

A compound according to Embodiment 1, wherein

A is N $R^1$ is selected from H; halogen; $C_6$-$C_{14}$ aryl; a 5 or 6-membered heterocyclic group, wherein the heterocyclic group contains at least one heteroatom selected from N, O and S; and $NR^{11}R^{12}$, wherein the aryl and heterocyclic groups are each optionally substituted by one or more Z substituents;

$R^2$ is $CF_3$;

$R^a$ is H;

$R^3$ is H or Me; and

E is $CR^7$.

Embodiment 10

A compound of Formula I which is selected from the following compounds:

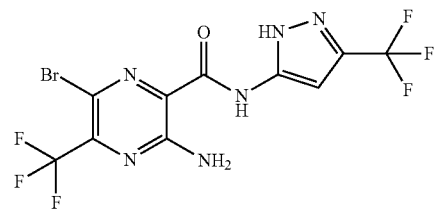

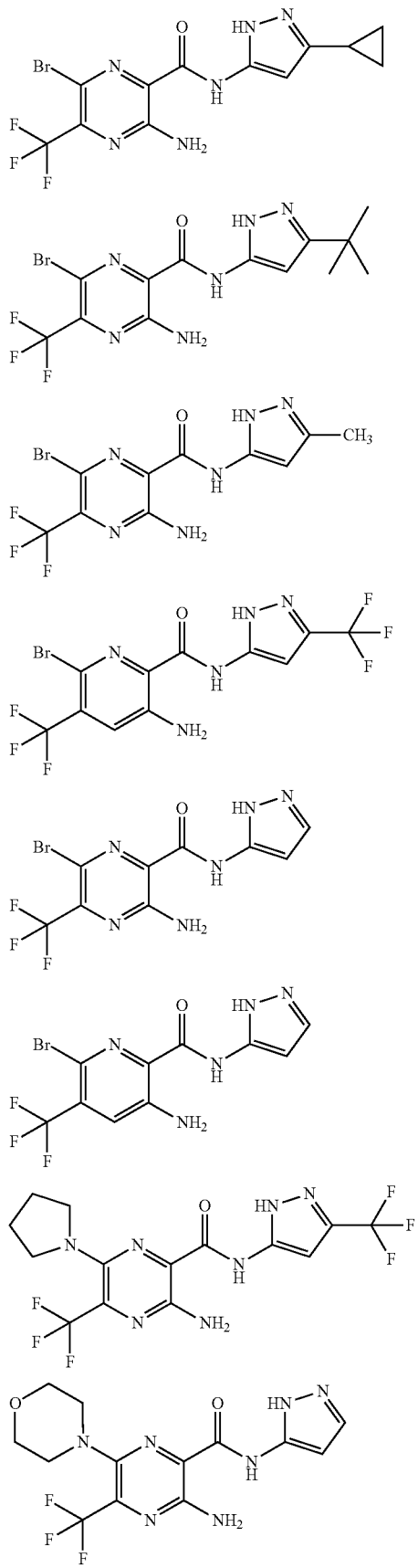
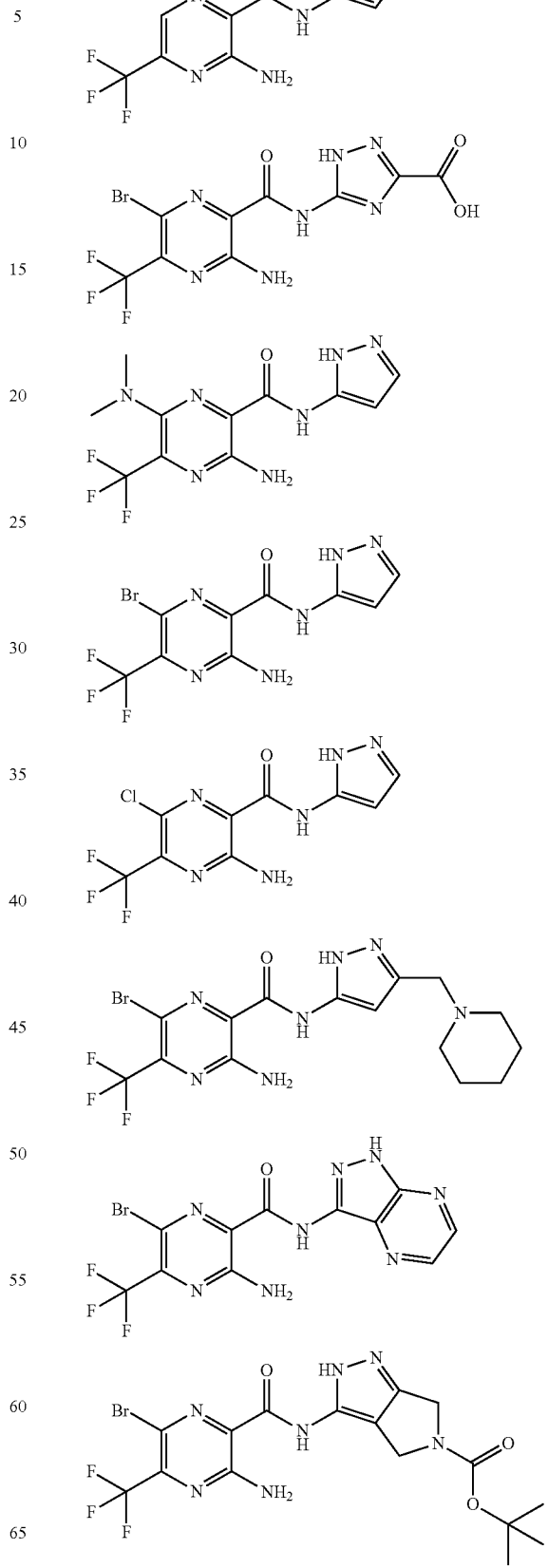

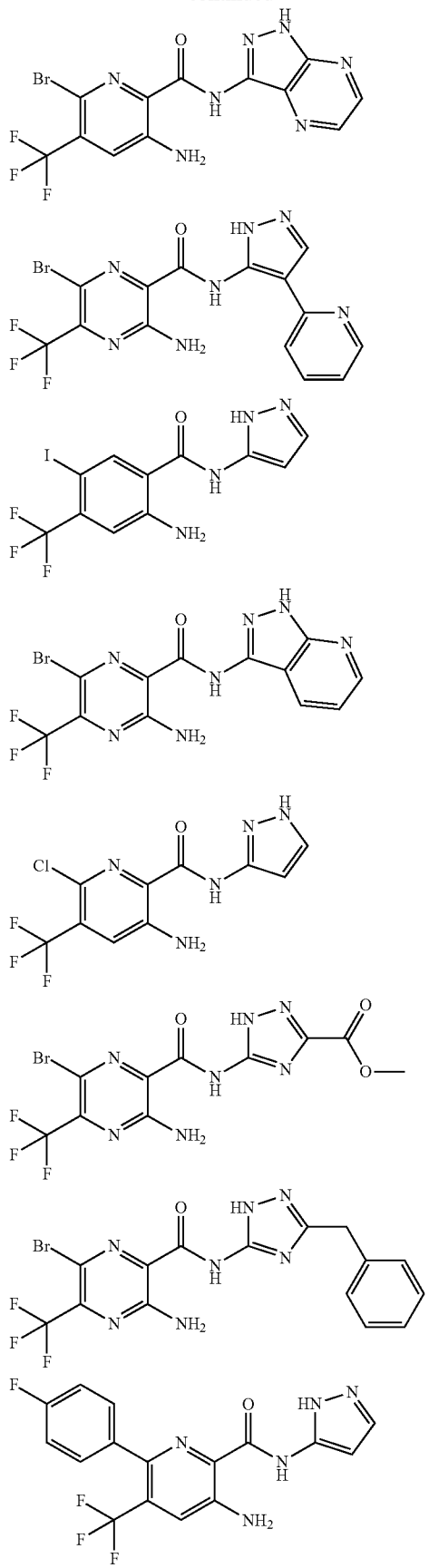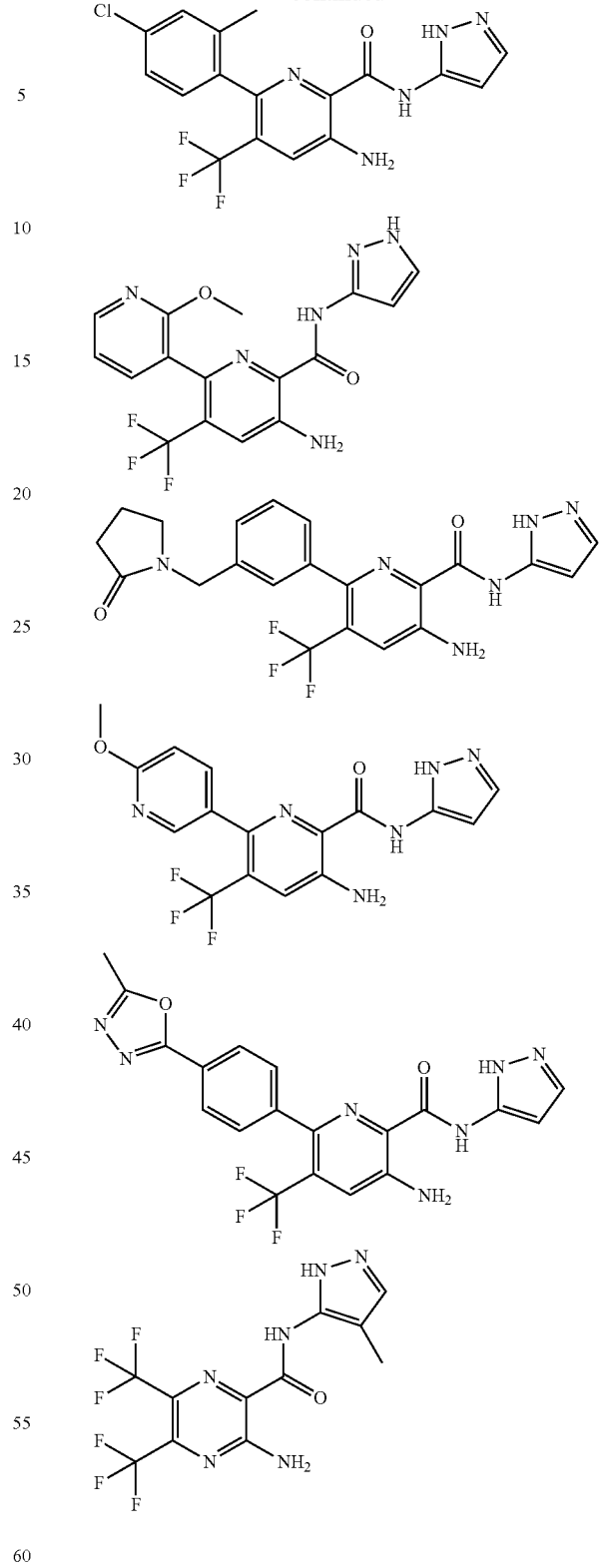
Embodiment 11
A compound of Formula I which is selected from the following compounds:
3-Amino-6-bromo-5-trifluoromethyl-pyrazine-2-carboxylic acid (5-trifluoromethyl-2H-pyrazol-3-yl)-amide;

3-Amino-6-bromo-5-trifluoromethyl-pyrazine-2-carboxylic acid (5-cyclopropyl-2H-pyrazol-3-yl)-amide;
3-Amino-6-bromo-5-trifluoromethyl-pyrazine-2-carboxylic acid (5-tert-butyl-2H-pyrazol-3-yl)-amide;
3-Amino-6-bromo-5-trifluoromethyl-pyrazine-2-carboxylic acid (5-methyl-2H-pyrazol-3-yl)-amide;
3-Amino-6-bromo-5-trifluoromethyl-pyridine-2-carboxylic acid (5-trifluoromethyl-2H-pyrazol-3-yl)-amide;
3-Amino-6-bromo-5-trifluoromethyl-pyrazine-2-carboxylic acid (2H-pyrazol-3-yl)-amide;
3-Amino-6-bromo-5-trifluoromethyl-pyridine-2-carboxylic acid (2H-pyrazol-3-yl)-amide;
3-Amino-6-pyrrolidin-1-yl-5-trifluoromethyl-pyrazine-2-carboxylic acid (5-trifluoromethyl-2H-pyrazol-3-yl)-amide;
3-Amino-6-morpholin-4-yl-5-trifluoromethyl-pyrazine-2-carboxylic acid (2H-pyrazol-3-yl)-amide;
3-Amino-5-trifluoromethyl-pyrazine-2-carboxylic acid (2H-pyrazol-3-yl)-amide;
5-[(3-Amino-6-bromo-5-trifluoromethyl-pyrazine-2-carbonyl)-amino]-1H-[1,2,4]triazole-3-carboxylic acid;
3-Amino-6-dimethylamino-5-trifluoromethyl-pyrazine-2-carboxylic acid (2H-pyrazol-3-yl)-amide;
3-Amino-6-bromo-5-trifluoromethyl-pyrazine-2-carboxylic acid (2H-[1,2,4]triazole-3-yl)amide;
3-Amino-6-chloro-5-trifluoromethyl-pyrazine-2-carboxylic acid (2H-pyrazole-3-yl)amide;
3-Amino-6-bromo-5-trifluoromethyl-pyrazine-2-carboxylic acid (5-piperidin-1-ylmethyl-2H-pyrazol-3yl)-amide;
3-Amino-6-bromo-N-(1H-pyrazolo[4,3-b]pyrazin-3-yl)-5-(trifluoromethyl)pyrazine-2-carboxamide;
tert-Butyl 3-(3-amino-6-bromo-5-(trifluoromethyl)pyrazine-2-carboxamido)-4,6-dihydropyrrolo[3,4-c]pyrazole-5(2H)-carboxylate;
3-Amino-6-bromo-N-(1H-pyrazolo[4,3-b]pyrazin-3-yl)-5-(trifluoromethyl)picolinamide;
3-Amino-6-bromo-N-(4-(pyridin-2-yl)-1H-pyrazol-5-yl)-5-(trifluoromethyl)pyrazine-2-carboxamide;
2-Amino-5-iodo-N-(1H-pyrazol-5-yl)-4-(trifluoromethyl)benzamide hydrochloride;
3-Amino-6-bromo-N-(1H-pyrazolo[3,4-b]pyridin-3-yl)-5-(trifluoromethyl)pyrazine-2-carboxamide;
3-Amino-6-chloro-N-(1H-pyrazol-5-yl)-5-(trifluoromethyl) picolinamide
Methyl 5-(3-amino-6-bromo-5-(trifluoromethyl)pyrazine-2-carboxamido)-1H-1,2,4-triazole-3-carboxylate;
3-Amino-N-(3-benzyl-1H-1,2,4-triazol-5-yl)-6-bromo-5-(trifluoromethyl)pyrazin-2-carboxamide;
3-Amino-6-(4-fluorophenyl)-N-(1H-pyrazol-3-yl)-5-(trifluoromethyl)picolinamide
3-Amino-6-(4-chloro-2-methyl-phenyl)-5-trifluoro methyl-pyridine-2-carboxylic acid (2H-pyrazol-3-yl)-amide;
5-Amino-2'-methoxy-3-trifluoro methyl-[2,3']bipyridinyl-6-carboxylic acid (1H-pyrazol-3-yl)-amide;
3-Amino-6-[3-(2-oxo-pyrrolidin-1-ylmethyl)-phenyl]-5-trifluoromethyl-pyridine-2-carboxylic acid (2H-pyrazol-3-yl)-amide;
5-Amino-6'-methoxy-3-trifluoromethyl-[2,3']bipyridinyl-6-carboxylic acid (2H-pyrazol-3-yl)-amide;
3-Amino-6-[4-(5-methyl-[1,3,4]oxadiazol-2-yl)-phenyl]-5-trifluoromethyl-pyridine-2-carboxylic acid (2H-pyrazol-3-yl)-amide;
3-Amino-5,6-bis-trifluoromethyl-pyrazine-2-carboxylic acid (4-methyl-2H-pyrazol-3-yl)-amide;
or a pharmaceutically acceptable salt or solvate thereof.

Embodiment 12

A compound of Formula I

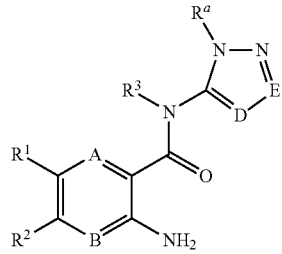

or a pharmaceutically acceptable salt or solvate thereof, wherein $R^1$, $R^2$, $R^3$, $R^a$, A, B, D and E are as defined in any of Embodiments 1 to 11 provided that either A or B, or both, is N.

Embodiment 13

A pharmaceutical composition comprising a therapeutically effective amount of a compound according to Embodiment 12 and one or more pharmaceutically acceptable carriers.

Embodiment 14

A combination comprising a therapeutically effective amount of a compound as defined in any of Embodiments 1 to 12 and one or more therapeutically active co-agents.

Embodiment 15

A combination according to Embodiment 14 wherein said co-agent is selected from osmotic agents, ENaC blockers, anti-inflammatory agents, bronchodilatory agents, antihistamine agents, anti-tussive agents, antibiotic agents and DNase drug substances, wherein the first and second actives may be in the same or different pharmaceutical composition.

Embodiment 16

A compound according Embodiment 12 for use as a medicament.

Embodiment 17

A compound according to any of Embodiments 1 to 12 for use in the treatment of a disorder or disease selected from an inflammatory or obstructive airways disease or mucosal hydration.

Embodiment 18

A compound according to any of Embodiments 1 to 12 for use in the treatment of a disorder or disease selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

Embodiment 19

Use of a compound as defined in any of Embodiments 1 to 12 in the manufacture of a medicament for use in the treatment of a disorder or disease of a disease or disorder mediated by CFTR.

Embodiment 20

Use of a compound as defined in any of Embodiments 1 to 12 in the manufacture of a medicament for use in the treatment of a disorder or disease selected from an inflammatory or obstructive airways disease or mucosal hydration.

Embodiment 21

Use of a compound as defined in any of Embodiments 1 to 12 in the manufacture of a medicament for use in the treatment of a disorder or disease selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

Embodiment 22

A method of treating a disease or disorder in a subject mediated by CFTR wherein the method comprises administering to the subject a therapeutically effective amount of the compound as defined in any of embodiments 1 to 12.

Embodiment 23

A method of modulating CFTR activity in a subject wherein the method comprises administering to the subject a therapeutically effective amount of the compound as defined in any of embodiments 1 to 12.

Embodiment 24

A method according to any of Embodiments 22 to 23 wherein the disorder or disease is selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

Embodiment 25

A pharmaceutical composition for treating disorder or disease mediated by CFTR comprising a compound according to any of Embodiments 1 to 12 as an active ingredient.

Embodiment 26

A pharmaceutical composition according to Embodiment 26 wherein the disorder or disease is selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

The invention claimed is:

1. A compound of Formula (I):

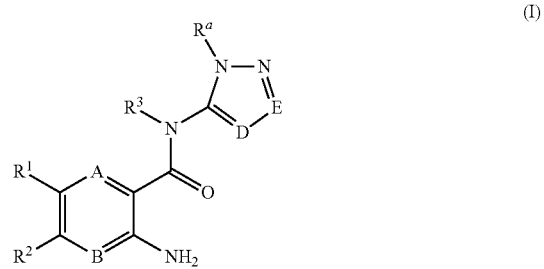

wherein:

A is N;

B is $CR^5$;

D is N or $CR^6$;

E is N or $CR^7$, provided that D and E are not both N;

$R^1$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; halogen; $SO_2NR^8R^9$; $SO_2R^{10}$; S—$C_1$-$C_8$ alkyl optionally substituted by one or more halogen atoms; S—$C_6$-$C_{14}$ aryl; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; CN; $NR^{11}R^{12}$; $CONR^{13}R^{14}$; $NR^{13}SO2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;

$R^2$ is selected from $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; Cl; Br; I; $SO_2NR^8R^9$; $SO_2R^{10}$; S—$C_1$-$C_8$ alkyl optionally substituted by one or more halogen atoms; S—$C_6$-$C_{14}$ aryl optionally substituted by one or more Z substituents; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; CN; $CONR^{13}R^{14}$; $NR^{13}SO2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;

$R^a$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $SO_2R^{10}$; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; $C(O)R^{15}$ and $CO_2R^{15}$, wherein the cycloalkyl, cycloalkenyl, aryl and heterocyclyl groups are each optionally substituted by one or more Z substituents;

$R^3$ and are each independently selected from H and $C_1$-$C_8$ alkyl optionally substituted by one or more halogen atoms;

$R^5$ is selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; halogen; —($C_0$-$C_4$ alkyl)-$C_6$-

$C_{14}$ aryl; and —($C_0$-$C_4$ alkyl)-3 to 14 membered heterocyclic group, wherein the heterocyclic group contains at least one heteroatom selected from N, O and S; wherein the cycloalkyl, cycloalkenyl, aryl and heterocyclyl groups are each optionally substituted by one or more Z substituents;

$R^6$ and $R^7$ are each independently selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; and —($C_0$-$C_4$ alkyl)-$CO_2R^{15}$, wherein the cycloalkyl, cycloalkenyl, aryl and heterocyclyl groups are each optionally substituted by one or more Z substituents; or $R^6$ and $R^7$ are each independently a group of the formula:

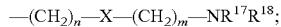
—$(CH_2)_n$—X—$(CH_2)_m$—$NR^{17}R^{18}$;

X is absent, O, S, CO, SO, $SO_2$ or $CH_2$;

n and m are each independently selected from 0, 1, 2 and 3;

$R^8$, $R^{11}$, $R^{13}$ and $R^{17}$ are each independently selected from H, $C_1$-$C_8$ alkyl optionally substituted by one or more halogen atoms, $C_3$-$C_{10}$ cycloalkyl and —($C_1$-$C_4$ alkyl)-$C_3$-$C_8$ cycloalkyl;

$R^9$, $R^{10}$, $R^{12}$, $R^{14}$, $R^{15}$ and $R^{18}$ are each independently selected from H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; and —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;

Z is independently selected from OH; aryl; O-aryl; benzyl; O-benzyl; $C_1$-$C_6$ alkyl optionally substituted by one or more OH groups or $NH_2$ groups; $C_1$-$C_6$ alkyl optionally substituted by one or more halogen atoms; $C_1$-$C_6$ alkoxy optionally substituted by one or more OH groups or $C_1$-$C_4$ alkoxy; $NR^{18'}(SO_2)R^{21}$; $(SO_2)NR^{19}R^{21}$; $(SO_2)R^{21}$; $NR^{18'}C(O)R^{21}$; $C(O)NR^{19}R^{21}$; $NR^{19}C(O)NR^{19}R^{21}$; $N^{18'}C(O)OR^{19}$; $NR^{19}R^{21}$; $C(O)OR^{19}$; $C(O)R^{19}$; $SR^{19}$; $OR^{19}$; oxo; CN; $NO_2$; halogen; and —($C_0$-$C_4$ alkyl)-3 to 14 membered heterocyclic group, wherein the heterocyclic group contains at least one heteroatom selected from N, O and S, optionally substituted by one or more groups selected from halogen, oxo, $C_1$-$C_6$ alkyl and $C(O)C_1$-$C_6$ alkyl;

$R^{18'}$ is independently selected from H and $C_1$-$C_6$ alkyl;

$R^{19}$ and $R^{21}$ are each independently selected from H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)- 3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl and $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl)$_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy;

or a pharmaceutically acceptable salt thereof.

2. A compound according to claim 1, wherein $R^1$ is selected from H; $C_1$-$C_8$ alkyl optionally substituted by one or more halogen atoms; halogen; $C_6$-$C_{14}$ aryl; —($C_0$-$C_4$ alkyl)-3 to 14 membered heterocyclic group, wherein the heterocyclic group contains at least one heteroatom selected from N, O and S; and $NR^{11}R^{12}$, wherein the aryl and heterocyclic groups are each optionally substituted by one or more Z substituents.

3. A compound according to claim 1, wherein $R^2$ is $C_1$-$C_8$ alkyl optionally substituted by one or more halogen atoms; $C_3$-$C_{10}$ cycloalkyl; or —$C_1$-$C_4$ alkyl-$C_3$-$C_8$ cycloalkyl.

4. A compound according to claim 3, wherein $R^2$ is $CF_3$.

5. A compound according to claim 1, wherein $R^3$ is H or methyl.

6. A compound according to claim 1, wherein E is $CR^7$.

7. A compound according to claim 1, wherein $R^1$ is selected from H; halogen; $C_6$-$C_{14}$ aryl; a 5 or 6-membered heterocyclic group, wherein the heterocyclic group contains at least one heteroatom selected from N, O and S; and $NR^{11}R^{12}$, wherein the aryl and heterocyclic groups are each optionally substituted by one or more Z substituents;

$R^2$ is $CF_3$;

$R^a$ is H;

$R^3$ is H or Me; and

E is $CR^7$.

8. A compound according to claim 1 selected from the following compounds:

3-Amino-6-bromo-5-trifluoromethyl-pyridine-2-carboxylic acid (5-trifluoromethyl-2H-pyrazol-3-yl)-amide;

3-Amino-6-bromo-5-trifluoromethyl-pyridine-2-carboxylic acid (2H-pyrazol-3-yl)-amide;

3-Amino-6-chloro-N-(1H-pyrazol-5-yl)-5-(trifluoromethyl)picolinamide;

3-Amino-6-(4-chloro-2-methyl-phenyl)-5-trifluoromethyl-pyridine-2-carboxylic acid (2H-pyrazol-3-yl)-amide;

3-Amino-6-[3-(2-oxo-pyrrolidin-1-ylmethyl)-phenyl]-5-trifluoromethyl-pyridine-2-carboxylic acid (2H-pyrazol-3-yl)-amide;

5-Amino-6'-methoxy-3-trifluoromethyl-[2,3']bipyridinyl-6-carboxylic acid (2H-pyrazol-3-yl)-amide; and 3-Amino-6-[4-(5-methyl-[1,3,4]oxadiazol-2-yl)-phenyl]-5-trifluoromethyl-pyridine-2-carboxylic acid (2H-pyrazol-3-yl)-amide;
or a pharmaceutically acceptable salt thereof.

9. A pharmaceutical composition comprising a therapeutically effective amount of a compound of claim 1 and one or more pharmaceutically acceptable carriers.

10. A method of treating a disease selected from cystic fibrosis or chronic obstructive pulmonary disease in a subject in need thereof, wherein the method comprises administering to the subject a therapeutically effective amount of the compound of claim 1.

* * * * *